US006365575B1

(12) United States Patent
Brigham et al.

(10) Patent No.: US 6,365,575 B1
(45) Date of Patent: *Apr. 2, 2002

(54) GENE DELIVERY AND EXPRESSION IN AREAS INACCESSIBLE TO DIRECT PROTEIN DELIVERY

(75) Inventors: Kenneth Brigham; Angelo Canonico; Barbara Meyrick; Arlene Stecenko, all of Nashville, TN (US)

(73) Assignee: Vanderbilt University, Nashville, TN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,552

(22) Filed: Oct. 16, 1997

Related U.S. Application Data

(60) Provisional application No. 60/029,252, filed on Oct. 24, 1996.

(51) Int. Cl.$^7$ .......................... A61K 48/00; C12N 15/12
(52) U.S. Cl. ......................................... 514/44; 536/23.5
(58) Field of Search ........................... 514/44; 536/23.5

(56) References Cited

U.S. PATENT DOCUMENTS

| 5,364,791 A | | 11/1994 | Vegeto et al. |
| 5,676,954 A | * | 10/1997 | Brigham |
| 5,756,353 A | * | 5/1998 | Debs |

FOREIGN PATENT DOCUMENTS

| WO | 92/19730 | 11/1992 |
| WO | 93/12240 | 6/1993 |
| WO | 93/12756 | 7/1993 |

OTHER PUBLICATIONS

Conary et al. Protection of Rabbit Lungs from Endotoxin Injury by In Vivo Hyperexpression of the Prostaglandin G/H Synthase Gene. J. Clinical Investigation vol. 93 pp. 1834–1840, 1994.*
Canonico et al. No lung toxicity after repeated aerosol or intravenous delivery of plasmid–cationic liposome complexes. J. Applied Physiology vol. 77 pp. 415–419, 1994.*
Kay et al. In Vivo Therapy of Hemophilia B: Sustained Partial Correction in Factor IX–Deficient Dogs. Science vol. 262 pp. 117–119, 1993.*
Tomlinson et al. Controllable gene therapy Pharaceutics of non–viral gene delivery systems. J. Controlled Release vol. 39 pp. 357–372, 1996.*
Orkin et al. Report and recommendations of the panel to assess the NIH investment in research on gene therapy. pp. 1–41, 1995.*
Korst et al. Gene therapy for the Respiratory Manifestations of Cystic Fibrosis. Am. J. Respir. Crit. Care Med. vol. 151 pp. 575–587, 1995.*

Johnson Gene Therapy for Cystic Fibrosis Chest vol. 107 pp. 77S–83S, 1995.*
McElvaney et al. Aerosol α1 antitrypsin treatment for cystic fibrosis. Lancet vol. 337 pp. 392–394, 1991.*
Brigham, K. et al., "Gene Therapy in Acute Critical Illness," *New Horizons* 3(2):321–329 (1995).
Canonico, A. et al., "Aerosol and Intravenous Transfection of Human α1–Antitrypsin Gene to Lungs of Rabbits," *Am. J. Respir. Cell Mol. Biol.* 10:24–29 (1994).
Bedard, M. et al., "Release of Interleukin–8, Interleukin–6, and Colony–stimulating Factors by Upper Airway Epithelial Cells: Implications for Cystic Fibrosis," *Am. J. Respir. Cell Mol. Biol.*, 9:455–462 (1993).
Boat, T.F. et al., "Cystic Fibrosis," *The Metabolic Basis of Inherited Disease.*, 2649–2680 (1989).
Campbell, E.J. et al., "Pericellular Proteolysis by Neutrophils in the Presence of Proteinase Inhibitors:Effects of Substrate Opsonization," *J. Cell Biol.* 106:667–676 (1988).
Canonico, A.E. et al., "Plasmid–Liposome Transfer of the $\alpha_1$ Antitrypsin Gene to Cystic Fibrosis Bronchial Epithelial Cells Prevents Elastase–induced Cell Detachment and Cytokine Release," *Am. J. Respir. Cell Mol. Biol.* 14:348–355 (1996).
Cantin, A.M. et al., "Antineutrophil Elastase Activity in Cystic Fibrosis Serum," *Pediatr. Pulmonol.* 11:249–253 (1991).
Cozens, A.L. et al., "Characterization of Immortal Cystic Fibrosis Tracheobronchial Gland Epithelial Cells," *Proc. Natl. Acad. Sci USA* 89:5171–5175 (1992).
Falk, W. et al., "A 48–Well Micro Chemotaxis Assembly for Rapid and Accurate Measurement of Leukocyte Migration," *J. Immunol. Methods* 33:239–247 (1980).
Hubbard, R.C. et al., "Fate of Aerosolized Recombinant DNA–Produced $\alpha_1$–antitrypsin: Use of the Epithelial Surface of the Lower Respiratory Tract to Administer Proteins of Therapeutic Importance," *Proc. Natl. Acad. Sci. USA* 86:680–684 (1989).
McCain, R. et al., "Granulocyte/Macrophage Colony–stimulating Factor Stimulates Human Polymorphonuclear Leukocytes to Produce Interleukin–8 In Vitro," *Am. J. Respir. Cell Mol. Biol.* 8:28–34 (1993).
McElvaney, N.G. et al., "Modulation of Airway Inflammation in Cystic Fibrosis," *J. Clin. Invest.* 90:1296–1301 (1992).
McElvaney, N.G. et al., "Aerosol α1–Antitrypsin Treatment for Cystic Fibrosis," *Lancet* 337:392–394 (1991).

(List continued on next page.)

*Primary Examiner*—John S. Brusca
(74) *Attorney, Agent, or Firm*—Needle & Rosenberg, P.C.

(57) ABSTRACT

The present invention provides novel methods for gene delivery and expression in areas that are currently inaccessible through the use of conventional direct protein delivery techniques. In particular, the methods and related products provided herein can be used in the treatment of $\alpha_1$ antitrypsin (AAT) related disorders such as respiratory syncytial virus (RSV) infection.

7 Claims, 12 Drawing Sheets

OTHER PUBLICATIONS

Meyer, K.C. et al., "Studies of Bronchoalveolar Lavage Cells and Fluids in Pulmonary Sarcoidosis," *Am. Rev. Resp. Disease* 140:1446–1449 (1989).

Nakamura, H. et al., "Neutrophil Elastase in Respiratory Epithelial Lining Fluid of Individuals with Cystic Fibrosis Induces Interleukin–8 Gene Expression in a Human Bronchial Epithelial Cell Line" *J. Clin. Invest.*, 89:1478–1484, (1992).

Persmark, M. et al., "Inhibition of Respiratory Syncytial Virus (RSV) Infectivity by Liposome–Mediated Antiprotease Gene Transfer" *J. Investig. Med.* 43 S:220A (1995).

Richman–Eisenstat, J.B.Y. et al., "Interleukin–8: an Important Chemoattractant in Sputum of Patients with Chronic Inflammatory Airway Diseases" *Am. J. Phys.*, 264:L413–L418 (1993).

Ruef, C. et al., "Regulation of Cytokine Secretion by Cystic Fibrosis Airway Epithelial Cells," *Eur. Respir. J.* 6:1429–1436 (1993).

Suter, S. et al., "Levels of Free Granulocyte Elastase in Bronchial Secretions from Patients with Cystic Fibrosis: Effect of Antimicrobial Treatment Against *Pseudomonas Aeruginosa*," *J. Infect. Dis.* 153:902–909 (1986).

Suter, S. et al., "Proteolytic Inactivation of $\alpha_1$–Proteinase Inhibitor in Infected Bronchial Secretions from Patients with Cystic Fibrosis," *Eur. Respir. J.* 4:40–49 (1991).

Uglea, C.V. et al., "Medical Applications of Synthetic Oligomers," *Polymeric Biomaterials* 725–747 (1993).

* cited by examiner

GENE DELIVERY AND EXPRESSION IN AREAS INACCESSIBLE TO DIRECT PROTEIN DELIVERY

RELATED APPLICATIONS

This application relates to U.S. patent application Ser. No. 60/029,252, filed Oct. 24, 1996, entitled "GENE DELIVERY AND EXPRESSION IN AREAS INACCESSIBLE TO DIRECT PROTEIN DELIVERY" by Brigham et al. which is incorporated herein by reference in its entirety, including any drawings.

INTRODUCTION

The present invention provides novel methods for gene delivery and expression in areas that are currently inaccessible through the use of conventional direct protein delivery techniques. In particular, the methods and related products provided herein can be used in the treatment of pulmonary disorders and delivery of anti-viral proteins.

BACKGROUND OF THE INVENTION

The following review of the background of the invention is merely provided to aid in the understanding of the present invention and neither it nor any of the references cited within it are admitted to be prior art to the present invention.

There are presently several approaches being studied for delivering genes to humans. These approaches have either: (i) removed somatic cells, permanently transformed them in vitro using retrovirus vectors, and reinfused the transformed cells; or (ii) used viruses to deliver the gene. Such therapy has been designed for use with patients having inherited deficiency of gene products, such as proteins, due to abnormalities of the gene during development. Such therapies have also been used with disorders such as emphysema, wherein it is thought that the disease process is a result of a relative deficiency of an antiprotease over a long period of time. Further, diseases such as acute lung injury resulting in the adult respiratory distress syndrome (ARDS) are thought to involve a relative deficiency of antiprotease activity. In addition, cystic fibrosis (CF) is the most common lethal genetic disease in Caucasians (Boat, T. F. et al., *The Metabolic Basis of Inherited Disease* 2649–2680, 1989). Even though CF can affect several organ systems, almost all patients develop chronic obstructive pulmonary disease and chronic pulmonary infections with resultant respiratory failure and early death.

Normally, the lung contains sufficient quantities of serine antiproteases, principally $\alpha_1$ antitrypsin ($\alpha_1 AT$), to combat the effects of toxic substances involved in such diseases, such as neutrophil elastase (NE). However, in CF and other neutrophil-dominated inflammatory lung diseases, the antiprotease defense system fails to prevent proteolytic damage to lung tissue (Boat, T. F. et al., *The Metabolic Basis of Inherited Disease* 2649–2680, 1989; Richman-Eisenstat, J. B. Y. et al., *Am. J. Phys.* 264: L413–L418, 1993).

One attempt at solving some of the above problems is described in International Patent Publication WO 92/19730 (hereby incorporated in its entirety, including any drawings) which describes means for the delivery of a gene encoding human $\alpha_1$ antitrypsin to the lungs for expression of the human $\alpha_1$ antitrypsin capable of alleviating the enzyme deficiency. Further advances regarding cationic liposome mediated antiprotease gene transfer to reduce the infectivity of RSV in cultured cells is reported in M. Persmark et al., *J. Investig. Med.* 43 S:220, 1995 Other attempts to deliver particular genes to cells of the lung or airway are described in International Patent Applications with publication numbers WO 93/12756 and WO 93/12240, both of which are incorporated herein by reference in their entirety including any drawings.

Despite the progress and success that has been achieved by such attempts, there still remains a need for a general method to provide gene delivery and expression to areas currently inaccessible to direct protein delivery. See R. C. Hubbard, et al. P.N.A.S. 86:680–684, 1989 (describing attempt to deliver protein via an aerosol and stating "In the present study, ≈1/500th of the administered dose was recoverable in lung lymph, a value likely too low to provide adequate protection for $\alpha_1$-antitrypsin deficiency"). Such obstacles have previously prevented the successful in vivo treatment of alpha antitrypsin (hereinafter "AAT") related disorders such as congenital AAT deficiency, as well as other disorders related to other proteins (for example, prostaglandin (hereinafter "PG") synthase see U.S. patent application Ser. No. 08/459,493, filed Jun. 2, 1995 incorporated herein by reference in its entirety including any drawings) that could not previously be treated by direct protein delivery to the desired target area using conventional methods of protein delivery.

SUMMARY OF THE INVENTION

The present invention is based in part on the surprising discovery that certain genes (preferred are genes encoding antiproteases such as AAT) can be delivered and expressed in vivo to certain target areas in animals (preferably mammals, more preferably humans) which have previously been inaccessible (i.e., an insufficient amount or inappropriate form of the protein is able to be provided to give a therapeutic response) to direct protein delivery.

A significant and unexpected advantage of the present invention is the ability of the delivered gene to provide a therapeutic response in situations where direct delivery of the protein (even when delivered at several fold higher serum concentrations) does not produce a therapeutic effect. In particular, delivery of the AAT gene has been found to essentially eliminate endotoxin induced increase in pulmonary vascular resistance, even when serum protein levels are approximately 20 fold lower than produced by protein delivery, which, (in contrast) produces no discernable effect on endotoxin response. In addition, delivery of the AAT gene is able to prevent respiratory syncytial virus infection of lung epithelial cells, where direct delivery of the encoded protein does not. Thus, such methods provide a method for successfully treating disorders caused by a deficiency of the product encoded by the gene of interest in the target area in the particular organism suffering from such a disorder.

The $\alpha_1$-antitrypsin protein is the major antiprotease in the lungs of humans. It is believed that both acute lung injury associated with inflammation and emphysema are a consequence of protease/antiprotease imbalance and increasing the antiprotease activity in the lungs is one possible approach to prevention and therapy of these conditions. In addition, there is a genetic form of $\alpha_1$-antitrypsin deficiency where patients develop emphysema at an early age.

Patients with $\alpha_1$-antitrypsin deficiency are now being treated with intravenous administration of the $\alpha$-antitrypsin protein. This intervention is expensive, requires relatively frequent intravenous infusions, can cause reactions in the patient and is of unproven efficacy. In addition, since the protein is derived from human blood products, a risk of infection by contaminating viruses, such as HIV is present.

Gene therapy by delivery of the DNA encoding $\alpha_1$-antitrypsin to the airway cells could provide a less invasive, safer, cheaper and more effective therapy.

Thus, in one aspect the invention provides a method for delivering a nucleic acid molecule to a location in an animal that is inaccessible to direct protein delivery. Those skilled in the art will understand that several conventional methods for directly delivering proteins exist and are commonly used in the art. The method involves the step of administering a positively charged liposome to the animal. The positively charged liposome is associated with the nucleic acid molecule, wherein said nucleic acid molecule is in operable association with a promoter. Those skilled in the art will recognize that a wide variety of promoters may be used to assist in targeting the desired location.

In preferred embodiments, the nucleic acid molecule encodes human $\alpha_1$ antitrypsin, the location is selected from the group consisting of an endothelial lung cell, a smooth muscle cells adjacent to the endothelial lung cell, and lung parenchyma, or the location is selected from the group consisting of a liver cell, a muscle cell, an osteogenic cell, synoviocyte, and a lung cell. Other preferred locations and genes are shown in Table I below.

TABLE I

| Clinical Indication | Gene | Target |
|---|---|---|
| Musculoskeletal | | |
| Muscle reconstruction and rehabilitation | IGF-1 | muscle |
| Cachexia (muscle wasting) | IGF-1, GH1 a HEH | muscle, liver |
| osteoporosis | calcitonin, IGF-1 | muscle |
| Arthritis | | |
| Osteoarthritis | nexin | joints |
| Gouty arthritic | urate oxidase | joints |
| Wound healing (dermal, epidermal) | FGF, EGF, TGFβ | skin |
| Muscular Dystrophy | Distrophin | muscle |
| Cardiovascular | | |
| Inotropic heart failure | IGF-1 | muscle |
| Hypertension | atrial naturetic factor | muscle |
| Atherogenes 15 | apo-A1, apo-B, | Liver |
| Hypercholesterolemia | apo-E, cholesterol | |
| | 7-α hydroxylase | Liver |
| | LDL receptor | Liver |
| | VLDL receptor | Liver |
| | lipoprotein lipase Liver | Liver |
| Restenosis injury | IFNα,k iNos, p53 | Smooth muscle |
| Homocystinermia | cystathione β-synthase | Liver, endothelium |
| Bleeding disorders | FACTORS VII & IX | MSV/Liver |
| Anemia | erythropoietin | MSV/Liver |
| Inflammation | | |
| Rheumatoid Arthritis | glucocortico-mimetic receptor | Joints |
| Inflammatory dermatitis (psoriasis) | TGFB | Skin |
| Inflammatory disease (systernic) | IL-1(RA), IL-1(SR)1 TGFB, TNF (SR) | muscle |
| Asthma | glucocortico-mimetic receptor | Alveolar macrophage |
| Glomerulonephritis | glucocortico-mimetic receptor | Kidney |
| Myositis | glucocortico-mimetic receptor | MSV |

TABLE I-continued

| Clinical Indication | Gene | Target |
|---|---|---|
| Bronchopulmonary dysplasia | superoxide dismutase | Lung |
| | gluathione reductase/peroxidase | Lung |
| Chronic active hepatitis | glucocortico-mimetic receptor | Liver |
| Cancer | | |
| Various turnors | IL-2, IL-12, IFNα, IFNγ, p53 | Tumor cells |
| Pulmonary | | |
| ARDS | AAT$_1$, PGH synthase, (Coα, Coα2) | Lung |
| Cystic Fibrosis | CFTR | Lung |

In other preferred embodiments the animal is a mammal, preferably a human, and the positively charged liposome is Lipofectin™. Other suitable liposomes are described in International Patent Application with publication numbers WO 93/12756 and WO 93/12240, both of which are incorporated by reference in their entirety, including any drawings. Preferably the nucleic acid sequence encodes a therapeutically effective protein (e.g., an antiprotease) and the method further involves expressing the nucleic acid sequence to provide the protein to the location.

In another aspect, the invention provides a method for preventing or treating an animal having a disorder. At least one symptom associated with the disorder is caused at least in part by an insufficient amount or form of protein in a particular location of the animal. The method involves the step of delivering a gene encoding the protein to the location and expressing the gene. Preferably at least 10%, more preferably at least 50%, most preferably at least 90% of the nucleic acid that is administered is delivered to said location.

In another aspect the invention provides a method for delivering a nucleic acid molecule to a location in an animal. The method involves the step of administering a positively charged liposome to the animal. The positively charged liposome is associated with the nucleic acid molecule, and the nucleic acid molecule is in operable association with a promoter. Delivery of the gene is capable of producing a therapeutic response, but direct delivery of the protein encoded by the gene does not produce a therapeutic response.

In preferred embodiments, delivery of the gene produces a therapeutic response even when delivered at a 10-fold lower serum concentration than the protein (which does not produce a therapeutic response when delivered directly as a protein). Preferably, the therapeutic response is elimination of an endotoxin induced increase in pulmonary vascular resistance.

In another aspect, a method of producing an elevated therapeutic response relative to the therapeutic response created by direct delivery of a protein. The method involves the step of delivering a nucleic acid molecule encoding the protein.

In preferred embodiments, the therapeutic response created by direct delivery of the protein is non-existent or immeasurable, and the protein is an antiprotease. Preferably, the enhanced therapeutic response is created in a patient suffering from a disorder selected from the group consisting of adult respiratory distress syndrome, cystic fibrosis, respiratory syncytial virus infection, and chronic obstructive pulmonary disease.

The composition is preferably capable of delivering the nucleic acid or oligonucleotide into a cell. By "delivering the nucleic acid or oligonucleotide into a cell" is meant transporting a complexed and condensed nucleic acid or a complexed oligonucleotide in a stable and condensed state through the membrane of a cell (in vitro or in vivo), thereby transferring the nucleic acid or oligonucleotide from the exterior side of the cell membrane, passing through the lipid bilayer of the cell membrane and subsequently into the interior of the cell on the inner side (i.e., cytosol side) of the cell membrane and releasing the nucleic acid or oligonucleotide once within the cellular interior.

In a preferred embodiment at least 1% of the nucleic acid or oligonucleotide in the composition is delivered into the cell or cells of the desired target location. In a more preferred embodiment, at least 10% of the nucleic acid or oligonucleotide is so delivered. In an even more preferred embodiment, at least 50% of the nucleic acid or oligonucleotide is so delivered. In a most preferred embodiment, at least 90% of the nucleic acid or oligonucleotide is so delivered.

Furthermore, the composition may prevent lysosomal degradation of the nucleic acid by endosomal lysis. In addition, although not necessary, the composition may also efficiently transport the nucleic acid through the nuclear membrane into the nucleus of a cell.

By "nucleic acid" is meant both RNA and DNA including: cDNA, genomic DNA, plasmid DNA, antisense molecule, polynucleotides or olignucleotides, RNA or mRNA. In a preferred embodiment, the nucleic acid administered is plasmid DNA which comprises a "vector".

By "vector" is meant a nucleic acid molecule incorporating sequences encoding polypeptide product(s) as well as, various regulatory elements for transcription, translation, transcript stability, replication, and other functions as are known in the art and as described herein. Vector can include expression vector.

An "expression vector" is a vector which allows for production or expressing a product encoded for by a nucleic acid sequence contained in the vector. The product may be a protein or a nucleic acid such as an mRNA which can function as an antisense molecule.

A "transcript stabilizer" is a sequence within the vector which contributes to prolonging the half life (slowing the elimination) of a transcript.

A "DNA vector" is a vector whose native form is a DNA molecule. By "non-viral" is meant any vector or composition which does not contain genomic material of a viral particle.

An "antisense molecule" can be a mRNA or an oligonucleotide which forms a duplex with a complementary nucleic acid strand and can prevent the complementary strand from participating in its normal function within a cell. For example, expression of a particular growth factor protein encoded by a particular gene.

A "gene product" means products encoded by the vector. Examples of gene products include mRNA templates for translation, ribozymes, antisense RNA, proteins, glycoproteins, lipoproteins and phosphoproteins.

"Post-translational processing" means modifications made to the expressed gene product. These may include addition of side chains such as carbohydrates, lipids, inorganic or organic compounds, the cleavage of targeting signals or propeptide elements, as well as the positioning of the gene product in a particular compartment of the cell such as the mitochondria, nucleus, or membranes. The vector may comprise one or more genes in a linear or circularized configuration. The vector may also comprise a plasmid backbone or other elements involved in the production, manufacture, or analysis of a gene product. The nucleic acid may be associated with a targeting ligand to effect targeted delivery.

A "targeting ligand" is a component of the delivery system or vehicle which binds to receptors, with an affinity for the ligand, on the surface or within compartments of a cell for the purpose of enhancing uptake or intracellular trafficking of the vector. Glucans such as Tris-galactosyl residues, carnitine derivatives, mannose-6-phosphate, monoclonal antibodies, peptide ligands, and DNA-binding proteins represent examples of targeting ligands which can be used to enhance uptake.

"Intracellular trafficking" is the translocation of the vector within the cell from the point of uptake to the nucleus where expression of a gene product takes place. Alternatively, cytoplasmic expression of a nucleic acid construct utilizing, for example, a T7 polymerase system may be accomplished. Various steps in intracellular trafficking include endosomal release and compartmentalization of the vector within various extranuclear compartments, and nuclear entry.

"Endosomal release" is the egress of the vector from the endosome after endocytosis. This is an essential and potentially rate limiting step in the trafficking of vectors to the nucleus. A lytic peptide may be used to assist in this process.

A "lytic peptide" is a peptide which functions alone or in conjunction with another compound to penetrate the membrane of a cellular compartment, particularly a lysosomal or endosomal compartment, to allow the escape of the contents of that compartment to another cellular compartment such as the cytosolic and/or nuclear compartment.

"Compartmentalization" is the partitioning of vectors in different compartments within a defined extracellular or intracellular space. Significant extracellular compartments may include, for example, the vascular space, hair follicles, interstitial fluid, synovial fluid, cerebral spinal fluid, thyroid follicular fluid. Significant intracellular compartments may include endosome, potosome, lysosome, secondary lysosome, cytoplasmic granule, mitochondria, and the nucleus.

"Nuclear entry" is the translocation of the vector across the nuclear membrane into the nucleus where the gene may be transcribed.

"Elimination" is the removal or clearance of materials (vectors, transcripts, gene products) from a specific compartment over time. This term may be used to reflect elimination from the body, the vascular compartment, extracellular compartments, or intracellular compartments. Elimination includes translocation (excretion) from a particular compartment or biotransformation (degradation).

The compounds which increase the efficacy of transfection of a nucleic acid are suitable for internal administration. By "suitable for internal administration" is meant that the compounds are suitable to be administered within the tissue of an organism, for example within a muscle or within a joint space, intradermally or subcutaneously. Other forms of administration which may be utilized are topical, oral, pulmonary, nasal and mucosal; for example, buccal, vaginal or rectal. These substances may be prepared as solutions, suspensions, gels, emulsions or microemulsions. Oil suspensions of lyophilized nucleic acid, such as plasmid DNA may be utilized. Delivery systems for these oil suspensions include, but are not limited to, sesame oil, cottonseed oil, soybean oil, lecithins, Tweens, Spans and Miglyols.

By "solutions" is meant water soluble substances and/or surfactants in solution with nucleic acids. By "suspensions" is meant water insoluble oils containing suspended nucleic acids. By "gels" is meant high viscosity substances containing nucleic acids. By "emulsion" is meant a dispersed system containing at least two immiscible liquid phases. Emulsions usually have dispersed particles in the 0.1 to 100 micron range. They are typically opaque and thermodynamically unstable. Nucleic acids in the water phase can be dispersed in oil to make a w/o emulsion. This w/o emulsion can be dispersed in a separate aqueous phase to yield a w/o/w emulsion. Alternatively, a suitable oil could be dispersed in an aqueous phase to form an o/w emulsion.

A "microemulsion" has properties intermediate to micelles and emulsions and is characterized in that they are homogenous, transparent and thermodynamically stable. They form spontaneously when oil, water, surfactant and co-surfactant are mixed together. Typically, the diameter of the dispersed phase is 0.01 to 0.1 microns, usually of the w/o and o/w type. The sustained-release compound containing a nucleic acid is administered to the tissue of an organism, for example, by injection. In one embodiment the tissue is preferably muscle tissue. In another embodiment the tissue is preferably a joint space.

By "sustained-release compound" is meant a substance with a viscosity above that of an isotonic saline solution (150 mM NaCl) containing a nucleic acid; for example, DNA in saline at 1 mg/ml has a viscosity of 3.01 mPa·sec, DNA in saline at 2 mg/ml has a viscosity of 3.26 mPa·sec, DNA in saline at 3 mg/ml has a viscosity of 5.85 mPa·sec (Viscosity measurements were performed at 25° C. in a Brookfield DV-III Rheometer with a No. 40 Spindle at 75 rpm for 30 minutes). Preferably the sustained-release compound has a viscosity in the range of about 0.1–20,000 mPa·sec above that of a complexation in which isotonic saline is the delivery system for a nucleic acid. More preferably the range is about 0.1–5000 mPa·sec above that of a complexation in which isotonic saline is the carrier for a nucleic acid. Even more preferably the range is about 0.1–1000 mpa·sec above that of a complexation in which isotonic saline is the carrier for a nucleic acid.

"Targeted delivery" involves the use of targeting ligands which specifically enhance translocation of a nucleic acid to specific tissues or cells. A "target" is a specific organ, tissue, or cell for which uptake of a vector and expression of a gene product is intended. "Uptake" means the translocation of the vector from the extracellular to intracellular compartments. This can involve receptor mediated processes, fusion with cell membranes, endocytosis, potocytosis, pinocytosis or other translocation mechanisms. The vector may be taken up by itself or as part of a complex. "Binding" is an intermediate step in uptake of some compositions involving a high-affinity interaction between a targeting ligand and a surface receptor on a target cell.

By "oligonucleotide" is meant a single-stranded polynucleotide chain. In a preferred embodiment, the oligonucleotide is less than 100 residues in length. In a more preferred embodiment, the oligonucleotide is less than 50 residues in length. In a most preferred embodiment, the oligonucleotide is less than 30 residues in length.

In a preferred embodiment, the invention features a composition capable of complexing and condensing the nucleic acid or oligonucleotide. These compositions provide smaller, or condensed, and more stable nucleic acid particles for delivery, thereby enhancing the transfection rate of nucleic acid into the cell and the subsequent expression therein.

By "complexing" is meant a high affinity interaction, based upon non-covalent binding, between the chitosan-based substance and the nucleic acid or oligonucleotide. By "affinity" is meant the selective tendency of elements to combine with one, rather than another element, when the physicochemical conditions are appropriate. This interaction is most preferably an ionic interaction but may be brought about wholly or in part by hydrogen bonding, Van der Walls interactions or other chemical attractions commonly recognized by those in the art. The compounds which complex and condense a nucleic acid may also interact or associate with the nucleic acid by intermolecular forces and/or valence bonds such as: Van der Waals forces, ion-dipole interactions, ion-induced dipole interactions, hydrogen bonds, or ionic bonds.

These interactions may serve the following functions: (1) Stereo selectively protect nucleic acids from nucleases by shielding; (2) facilitate the cellular uptake of nucleic acid by "piggyback endocytosis". By "piggyback endocytosis" is meant the cellular uptake of a drug or other molecule complexed to a delivery system that may be taken up by endocytosis (C. V. Uglea and C. Dumitriu-Medvichi, *Medical Applications of Synthetic Oligomers*. In: "Polymeric Biomaterials." Edited by Severian Dumitriu. Marcel Dekker, Inc. 1993) and incorporated herein by reference including all drawings and figures. To achieve the desired effects set forth, it is desirable, but not necessary, that the substances which condense and complex nucleic acid have amphipathic properties; that is, the substance has both hydrophilic and hydrophobic regions. The hydrophilic region of the substance may associate with the largely ionic and hydrophilic regions of the nucleic acid, while the hydrophobic region of the substance may act to retard diffusion of nucleic acid and to protect nucleic acid from nucleases. Additionally, the hydrophobic region may specifically interact with cell membranes, possibly facilitating endocytosis of the composition and thereby nucleic acid associated with the compound. This chitosan-based composition may increase the pericellular concentration of nucleic acid.

By "condensing" is meant charge neutralization, exclusion of water and compacting into colloidal particles. The composition which condense and complex nucleic acid may also achieve one or more of the following effects, due to their physical, chemical or rheological properties: (1) Protect nucleic acid, for example plasmid DNA, from nucleases; (2) increase the area of contact between nucleic acid, such as plasmid DNA, through extracellular matrices and over cellular membranes, into which the nucleic acid is to be taken up; (3) concentrate nucleic acid, such as plasmid DNA, at cell surfaces due to water exclusion; (4) indirectly facilitate uptake of nucleic acid, such as plasmid DNA, either increasing interaction with cellular membranes and/or by perturbing cellular membranes due to osmotic, hydrophobic or lytic effects.

By "increase the efficacy of transfection" is meant that a nucleic acid or oligonucleotide when administered to an organism in a composition comprising such a substance will be more readily taken up into the interior of a cell by translocating across the cellular membrane than if administered in a composition without such a substance, for example when administered in a formulation such as a saline solution. The increased efficiency of uptake of nucleic acid, or oligonucleotide into cells could occur, for example, due to a better steric fit between the composition containing the nucleic acid and a pit on the surface of the cellular membrane or due to protection of the nucleic acid from attack by nucleases.

In another preferred embodiment, the composition has a net positive charge ratio. By "net charge" is meant the resulting positive, negative or neutral character of a compound which is determined after balancing the total number of positive and negative charges possessed by a molecule or compound. For example, the DNA molecule, has a net negative charge due to the presence of two anionic phosphate moieties on each base pair of the molecule. The number of negatively charged phosphates exceed in number the total number of positive charges on the DNA molecule. Thus the surfeit of negative charges imparts a net negative character or charge to DNA. The number of negative charges to positive charges on compositions determines the net charge ratio. The net charge ratio is symbolized by (−/+) where a dash, "−", stands for a negative charge and a plus sign, "+", stands for a positive charge. A net charge ratio of 1:1(−/+) is neutral; of 2:1(−/+) is negative and of 1:2(−/+) is positive.

Another embodiment features the composition additionally mixed with a cryoprotectant. By "cryoprotectant" is meant any chemical or compound which will serve to protect nucleic acid and oligonucleotides and the complexed particles during lyophilization, storage, and subsequent rehydration. Examples of "cryoprotectants" include, but are not limited to, such compounds as lactose, sucrose, mannitol, and trehalose.

In another aspect, the nucleic acid or oligonucleotide is delivered to a cell by the step of exposing the composition to the cell. The method may be performed in vitro, in vivo, or on a cell that has been removed from a living organism. If the method is performed in vivo, then the exposing step may be performed by administering the composition to an organism.

By "administering" is meant the route of introduction of the composition into a body. Administration can be directly to a target tissue or through systemic delivery. In particular, administration may be by direct injection to the cells. Routes of administration include, but are not limited to, intramuscular, aerosol, oral, topical, systemic, nasal, ocular, intraperitoneal and/or intratracheal, buccal, sublingual, oral, intradermal, subcutaneous, pulmonary, intra-artricular, and intra-arterial. In a preferred embodiment administration is by intravenous administration.

By "organism" is meant a living entity capable of replication. In a preferred embodiment the organism is an animal, in a more preferred embodiment a mammal, and in a most preferred embodiment a human.

Other features and advantages of the invention will be apparent from the following description of the preferred embodiments thereof and from the claims.

BRIEF DESCRIPTION OF THE DRAWINGS

FIG. 3a shows that following intravenous administration of the protein, AAT localizes to the endothelium (arrow). FIG. 3b shows following gene transfer, the AAT transgene product is seen in the endothelium, the adjacent smooth muscle cells, and the lung parenchyma (arrows).

DETAILED DESCRIPTION OF THE INVENTION

The present invention relates to a method for delivering a nucleic acid molecule to a location in an animal that is inaccessible to direct protein delivery. Such methods of delivery allow for new methods of treating and preventing disorders based on the deficiency of a certain protein in such a location. The sections below provide examples of particular genes that can be delivered to particular locations previously inaccessible via a direct protein delivery. This detailed disclosure also presents new diseased targets that are now treatable in view of the novel gene delivery methods reported herein. Especially preferred embodiments involving delivery of the AAT gene or prostaglandin synthase are also described in detail and will be better understood in view of the sections below.

I. AAT Gene Therapy Compared to Exogenous AAT Protein (Prolastin)

The AAT protein, Prolastin, is available and in clinical use and a number of other proteins have been suggested as therapeutics for various disorders. The present invention, however, demonstrates that certain locations (for example, the lung) might be better protected by protein AAT (for example, produced in the cells for which protection from proteolytic injury is needed, rather than by the protein delivered intravenously (or via the airways). Provided herein is experimental data substantiating that claim in cultured lung epithelial cells and in vivo in a pig endotoxin model. In particular, the data demonstrates that the location of AAT protein delivered intravenously is different than that produced as a consequence of in vivo gene delivery and that intravenously delivered protein is not capable of achieving the same therapeutic effect that is produced by the in vivo gene delivery.

II. AAT Gene Therapy Prevents Respiratory Syncytial Virus (RSV) Infection of Lung Epithelial Cells, but Exogenous AAT (Prolastin) Does Not As is true for many viruses, cell surface and intracellular proteolytic events are involved in the ability of RSV to infect respiratory epithelial cells. The effects of transfecting an RSV susceptible lung epithelial cell line with the pCMV4AAT construct was determined using cationic liposomes on RSV infectivity. Effects of exogenous AAT added to the medium in a range of concentrations was also determined.

Figure 1:
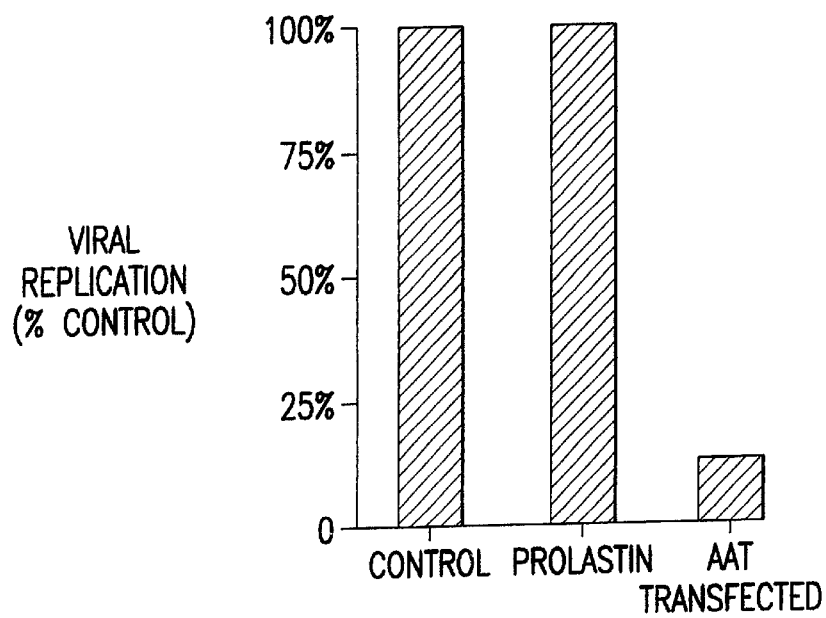
FIG. 1 shows the effects of AAT gene therapy vs. exogenous protein administration on Respiratory Syncytial Virus (RSV) replication. Transfection with the AAT gene 48 hours before RSV infection significantly reduced RSV replication. AAT protein added to the medium in amounts 50–100 times that achieved with AAT gene therapy had no effect on RSV replication.

Transfection with the AAT plasmid resulted in maximal levels of AAT in the medium of 300–800 ng/ml. FIG. 1 shows viral replication in the cell line studied as plaque forming units (PFU) in cells which received no treatment, cells exposed to RSV after transfection with AAT and cells exposed to exogenous AAT at a concentration of 30,000 ng/ml in the medium. The effects of the exogenous protein and transfection with the AAT gene were substantially different. Transfection with AAT markedly reduced RSV infectivity, but exogenous protein had little effect.

III. AAT Gene Therapy Prevents Endotoxin Induced Lung Toxicity in Piglets, but Exogenous AAT (Prolastin) Does Not Antiproteases, specifically AAT, have been suggested as potential therapy for acute lung injury, but experimental efficacy studies of with the exogenous protein have not been very convincing. The present invention unexpectedly demonstrates that AAT gene therapy is significantly more effective than the exogenous protein as assessed in a piglet endotoxin model.

In young pigs (3–5 kg), the effects of in vivo transfection with the pCMV4AAT construct using cationic liposomes delivered intravenously was compared to the effects of AAT protein (Prolastin) added to the circulation. 48 hours prior to endotoxin administration, PCMV4AAT was delivered at a dose of 1 mg/kg body weight complexed in a 1:3 (w:w) ratio with DOTMA/DOPE liposomes (Lipofectin) by slow intravenous infusion. Results of the endotoxin studies were compared with results from two other study groups. One group received only endotoxin and the other group received Prolastin one hour prior to endotoxin infusion. To study the effects of endotoxin, an in situ perfused lung preparation (where blood flow is kept constant and pulmonary vascular pressures are measured was used.

Figure 2:
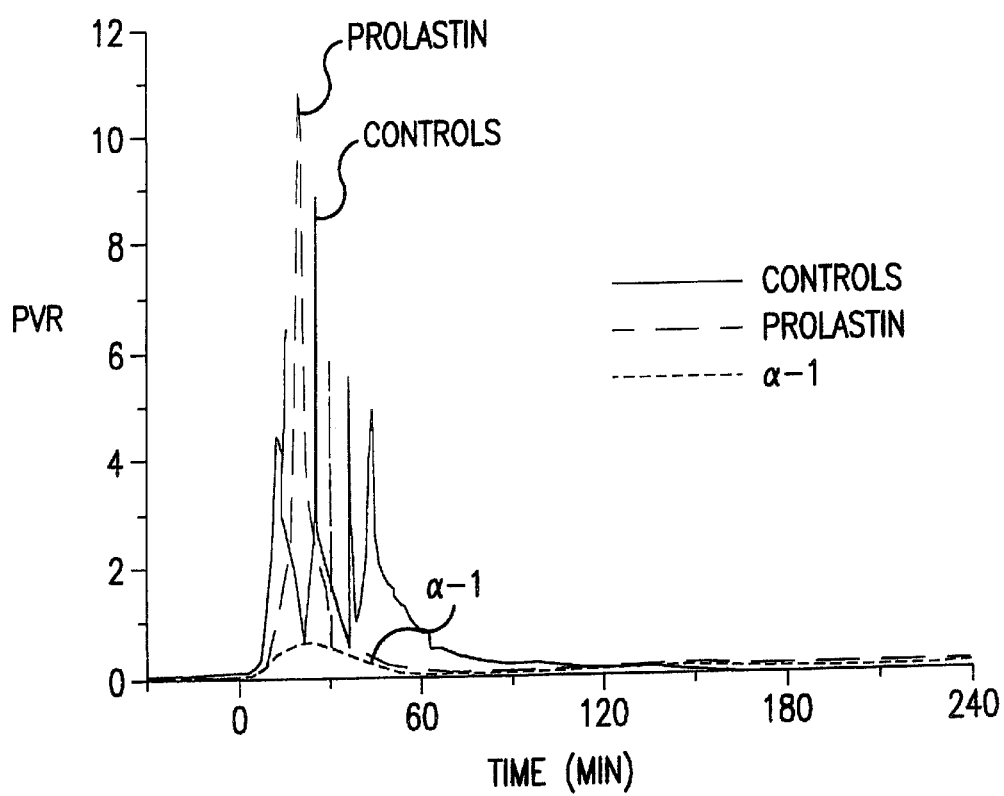
FIG. 2 shows pulmonary vascular resistance (PVR) normalized to baseline following endotoxin exposure in a piglet in situ lung preparation. Marked increase in PVR is seen in control piglets (i.e., endotoxin alone) and in piglets that received exogenous AAT protein before endotoxin. Intravenous transfection with the AAT transgene blocks this effect.

Following transfection with the AAT plasmid, measurable blood concentrations of human AAT ranging from 45.1–217.8 ng/ml (average 105.5 ng/ml) were consistently observed. Blood concentrations of AAT in the animals receiving Prolastin were in excess of 2000 ng/ml. Five animals received the AAT gene, five animals received the AAT protein, and six animals served as controls. FIG. 2 shows pulmonary vascular resistance (PVR) over the course of the endotoxin response in all three experimental groups. Each line is the mean data for the animals in each group. Addition of exogenous AAT had no discernible effect on the endotoxin response. Surprisingly, and in contrast, transfection with AAT essentially eliminated the endotoxin induced increase in PVR.

Figure 3A:
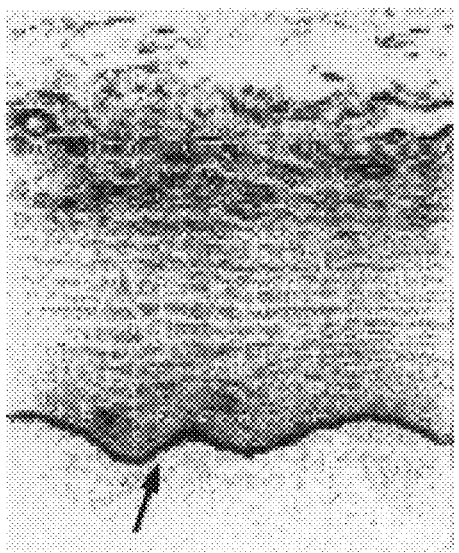
FIGS. 3A–3B shows immunohistochemical localization of human AAT in the pulmonary vasculature of the piglet.
Figure 3B:
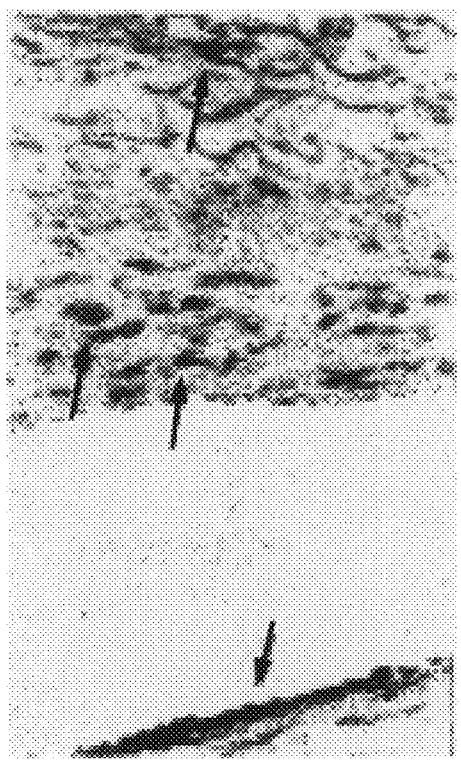

FIGS. 3A and 3B are photomicrographs showing immunohistochemical staining of human $\alpha_1$ antitrypsin in the lungs of pigs 48 hours after transfection with the AAT gene (FIG. 3A) and after intravenous infusion of Prolastin in the same concentrations as given in the physiologic studies (FIG. 3B). There are dramatic differences in the location of the protein. AAT generated as a consequence of gene therapy is located throughout the vascular wall and lung parenchyma, as well as on the surface of the endothelium. In contrast, delivery of AAT protein localizes to the vascular endothelium only; the exogenous protein does not penetrate beyond the endothelium.

To our knowledge, this is the first demonstration that protein such as AAT produced as a result of gene transfer is present in a markedly different physiological space than is the exogenous protein. It is also the first demonstration that the therapeutic potential of proteins (such as AAT and other antiproteases) produced as a consequence of gene transfer is dramatically different than that of the exogenous protein. These data indicate that gene therapy with AAT can achieve therapeutic concentrations of the protein in the plasma, since plasma levels are apparently irrelevant to some of the therapeutic effects achieved with AAT gene therapy.

IV. Delivery of the AAT Gene to Humans with AAT Deficiency

The AAT gene has now been delivered to the nasal epithelium of two human patients with AAT deficiency. This protocol involves removing the patients from Prolastin therapy for 1 month, collecting baseline nasal lavage samples on several occasions and then transfecting one nostril with the pCMV4AAT preparation using DOTMA/DOPE cationic liposomes. The untransfected nostril serves as the control. Following transfection, nasal lavage samples are collected periodically for a month and nasal inflammation is assessed by nasal scraping and staining of cells obtained in this manner. Blood samples are taken for general screening to determine if systemic distribution of the plasmid occurs.

Figure 4:
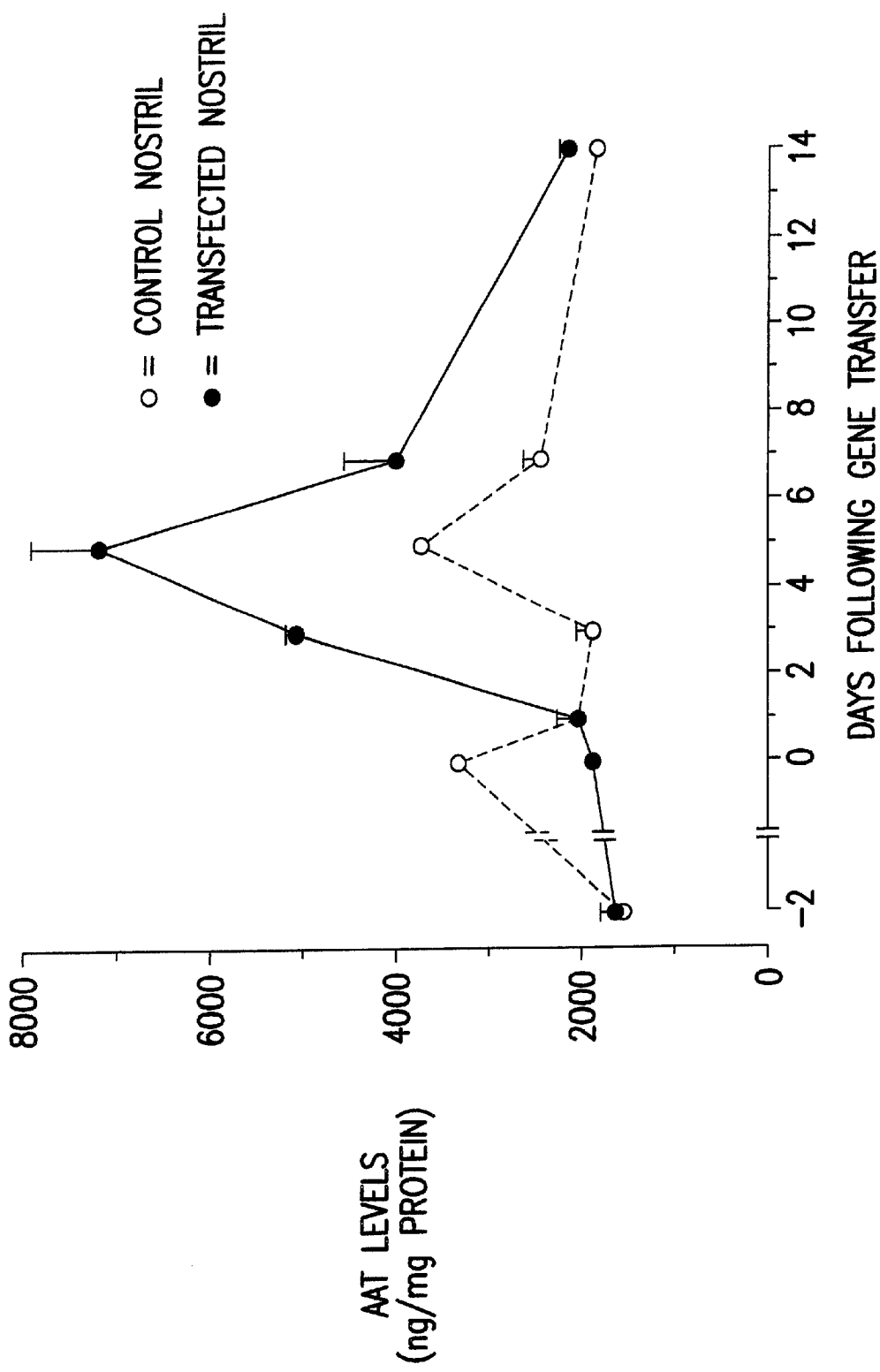
FIG. 4 shows expression of the $alpha_1$ antitrypsin transgene in the nasal mucosa of AAT deficient patients. Time course and expression of the AAT transgene.

The studies have presented no technical problems. No abnormalities in blood tests have been identified and nasal scrapings show no discernible effects of transfection as compared to the untransfected nostril. FIG. 4 shows concentrations of AAT measured by ELISA in the lavage from each nostril over time in the second patient studied. There is a convincing increase in AAT concentrations in the lavage fluid from the transfected nostril with no consistent change in the untransfected nostril.

Figure 5:
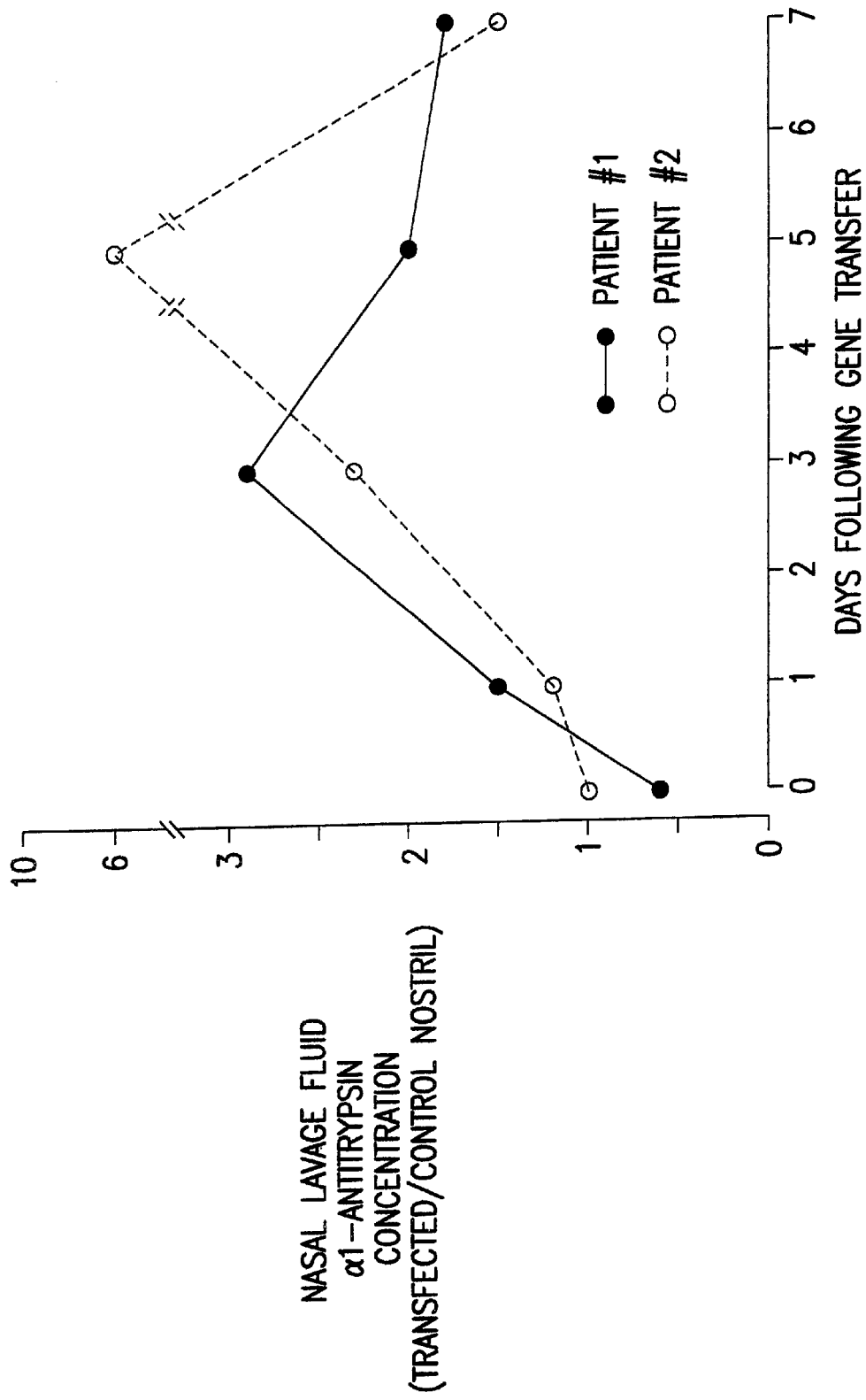
FIG. 5 shows expression of the $alpha_1$ antitrypsin transgene in the nasal mucosa of AAT deficient patents. Ratio of AAT protein levels in lavages from transfected vs. control nostril.

FIG. 5 summarizes the data from the two patients. It shows expression of the AAT transgene as the ratio of AAT concentration in the transfected nostril to that in the untransfected nostril in each of the two patients studied. In each case there is a convincing 3–6 fold increase in AAT in the transfected nostril peaking at 3–5 days, and remaining about twice baseline at 7 days. These data make a convincing case that the techniques of the present invention effectively delivers the transgene to the nasal mucosa. This clinical model thus appears ideal for testing different preparations, delivery strategies, and the consequences of in vivo gene delivery for the respiratory epithelium.

V. Disease Targets

There are several possible clinical targets for an AAT gene medicine in addition to AAT deficiency. In view of the data in the studies in piglets presented above, acute respiratory distress syndrome (ARDS) is a realistic disease target. Further, a dose ranging study in ARDS patients could be performed by those skilled in the art may using techniques that are standard and conventional in the art.

Patients with emphysema are another patient population that would also be a target for AAT gene therapy. Although not a consequence of a genetic AAT deficiency, the anatomy and physiology of the disease in the patients who are candidates for lung reduction are identical to patients with AAT deficiency. The most popular hypothesis for development of emphysema is that it results from a relative AAT deficiency (i.e. excessive protease burden). In view of the new data presented herein showing that AAT gene therapy is dramatically more effective than exogenous AAT protein an evaluation of AAT gene therapy in this group is easily justified. Extension to a broad group of patients with chronic obstructive pulmonary disease (COPD) may also be justified.

Respiratory infections with respiratory syncytial virus (RSV) are often lethal in immunocompromised patients, are a precipitating cause of respiratory failure in patients with COPD, and occur in annual epidemics in children. Thus, this a particularly attractive clinical target, since the disease starts in the nasal mucosa and AAT gene therapy could be targeted there.

VI. Development of a Prostaglandin Synthase Gene Medicine Studies in Chronically Instrumented Unanesthetized Sheep The present invention also provides an animal model in unanesthetized sheep for intravenous delivery of plasmid-liposome complexes. This animal model can be used to define the effects of the procedure on lung function, hemodynamics and general well-being of the animals. In addition, the sheep lung lymph preparation provides unique information relevant to the potential therapy for acute lung injury (i.e. ARDS).

The current study protocol calls for two endotoxin studies in each animal: One without PGH synthase gene transfection and the other 72 hours following transfection with the gene. The two studies must be done in random order in order to avoid historical bias of the endotoxin responses.

Paired studies in 2 sheep (4 studies) have been completed. In one of the animals, the PGH synthase gene was administered 72 hours prior to the initial endotoxin study. The second endotoxin study was repeated one week later. The other animal had a baseline endotoxin study performed before delivering the PGH synthase gene. One week later, the PGH synthase gene was administered and the endotoxin study repeated 72 hours after transfection.

Figure 6:
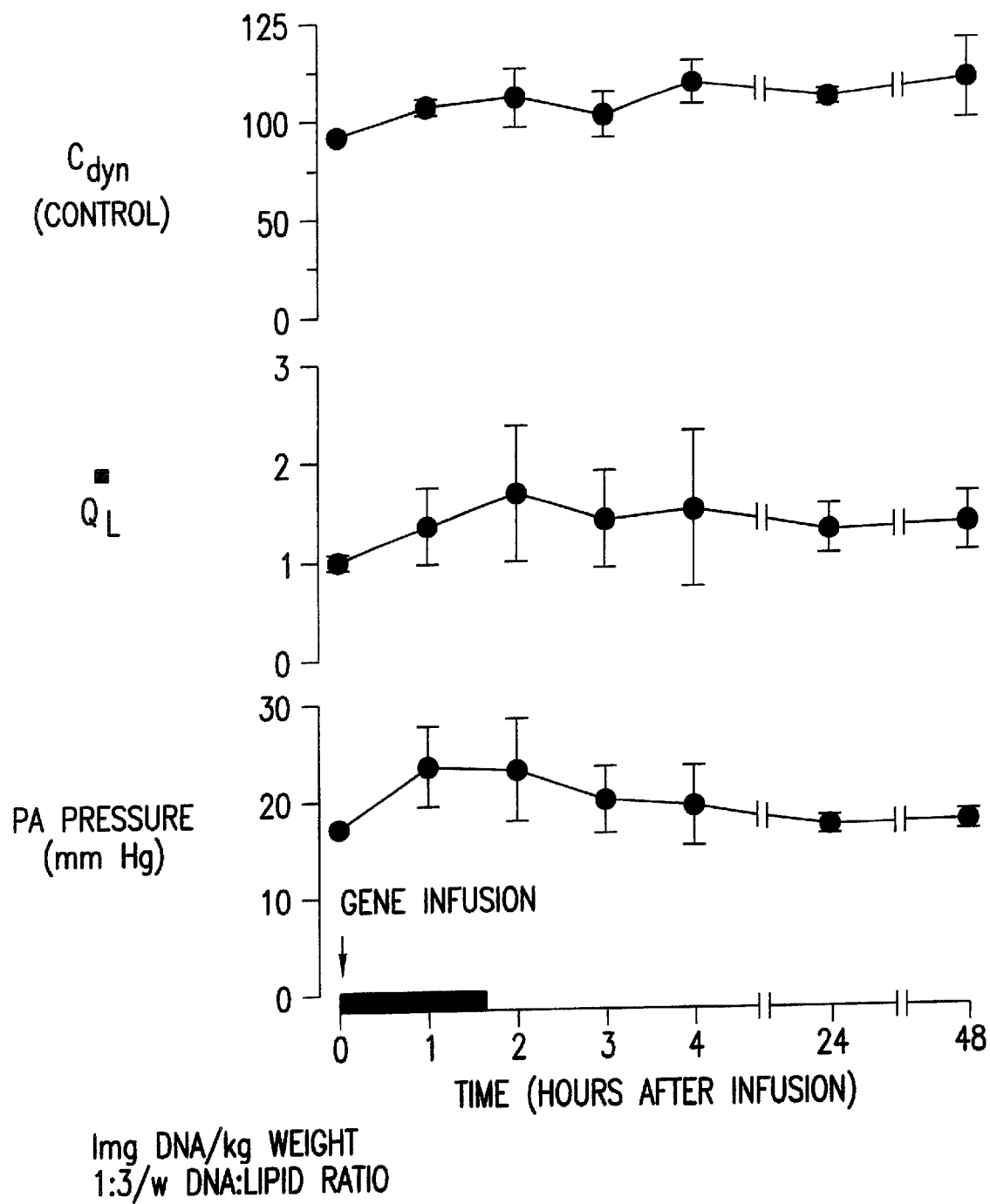
FIG. 6 shows the results of intravenous administration of plasmid-liposome complexes: There was no effect of plasmid-liposome compels infusion on lung mechanics ($C_{dyn}$) or lung lymph flow ($Q_L$) A transient rise in pulmonary artery pressure (PA Pressure) was seen which returned to baseline when the infusion was stopped.
Figure 7:
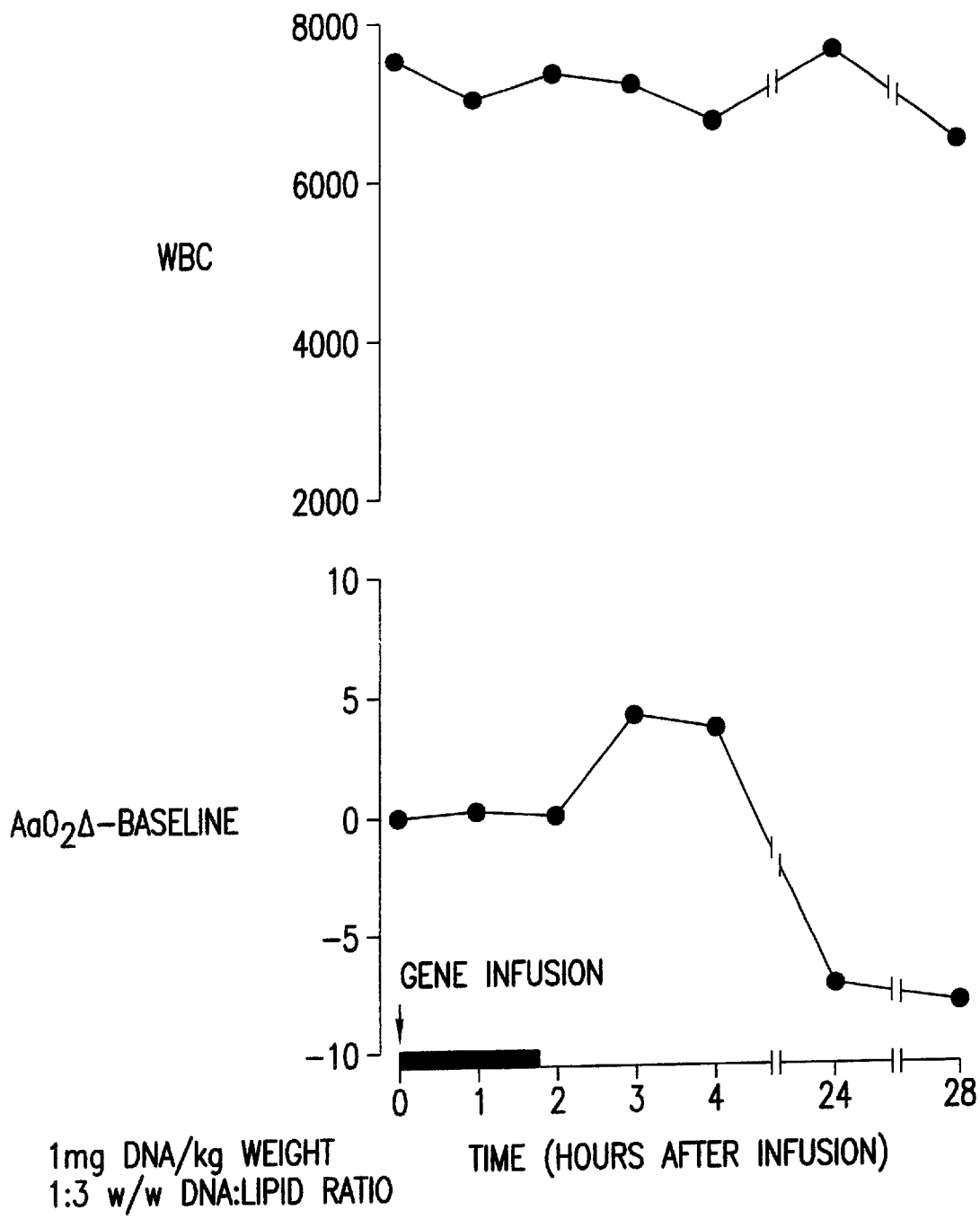
FIG. 7 shows the results of intravenous administration of plasmid-liposome complexes: There was no effect of plasmid-liposome complex infusion on white blood cell count (WBC) or oxygenation ($AaO_2A$-Baseline).

No ill effects of infusing the plasmid-liposome complexes were noted. FIG. 6 shows the effects of plasmid/liposome complex infusion on lung mechanics, lung lymph flow, and pulmonary artery pressure. FIG. 7 shows the effects of plasmid-liposome complex infusion on the white blood count and oxygenation. Plasmid-liposome complex infusion had no effect on blood cell counts, chemistries, lung mechanics, arterial blood gases or lung lymph flow. The only effect on physiology was a small rise in pulmonary artery pressure during the infusion. This was a transient rise and returned immediately to baseline when the infusion was stopped.

Figure 8:
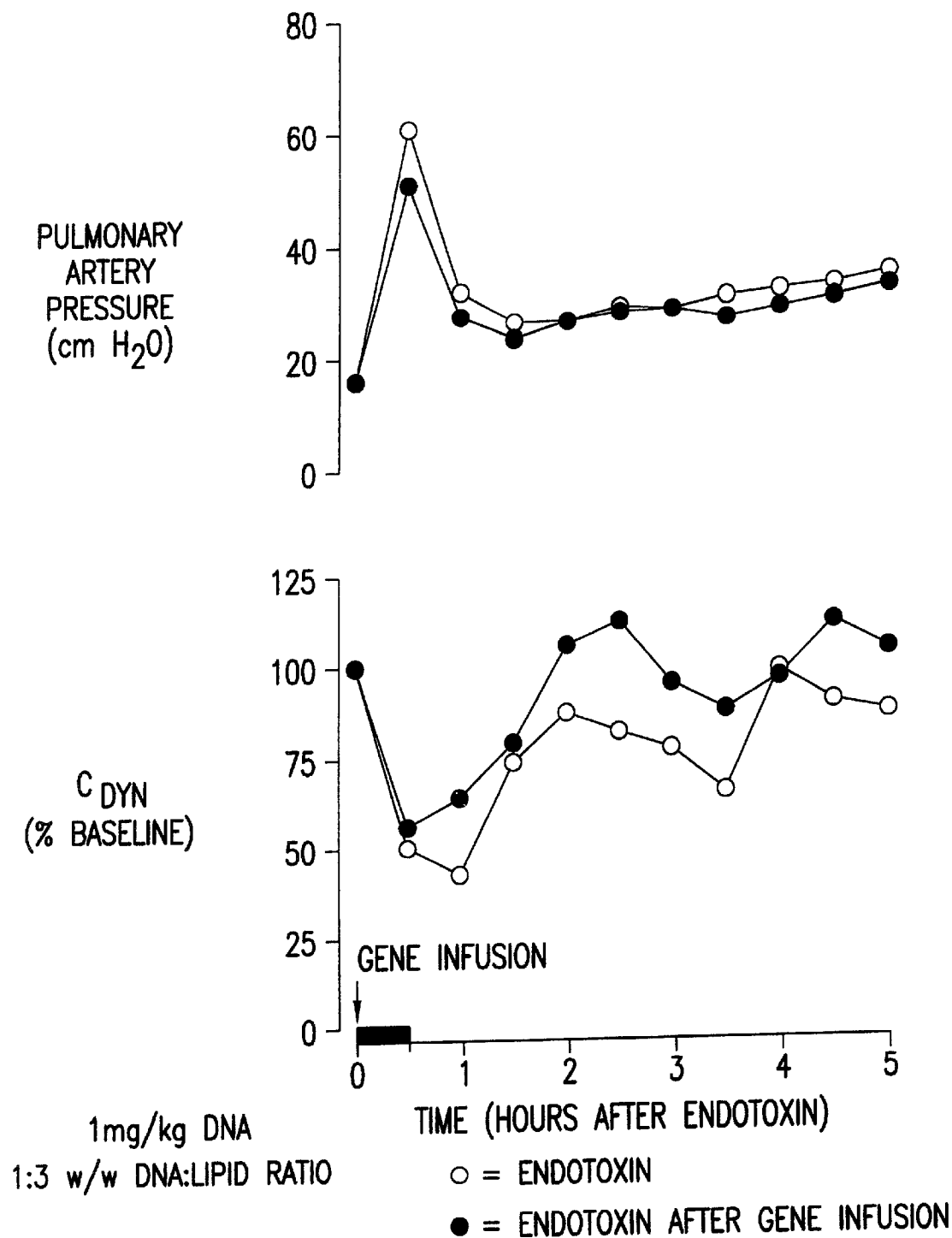
FIG. 8 shows the effects of endotoxin administration 72 hours after PGH synthase gene infusion: No effect on pulmonary artery pressure was seen. A persistent improvement in lung mechanics ($C_{dyn}$) was noted.
Figure 9:
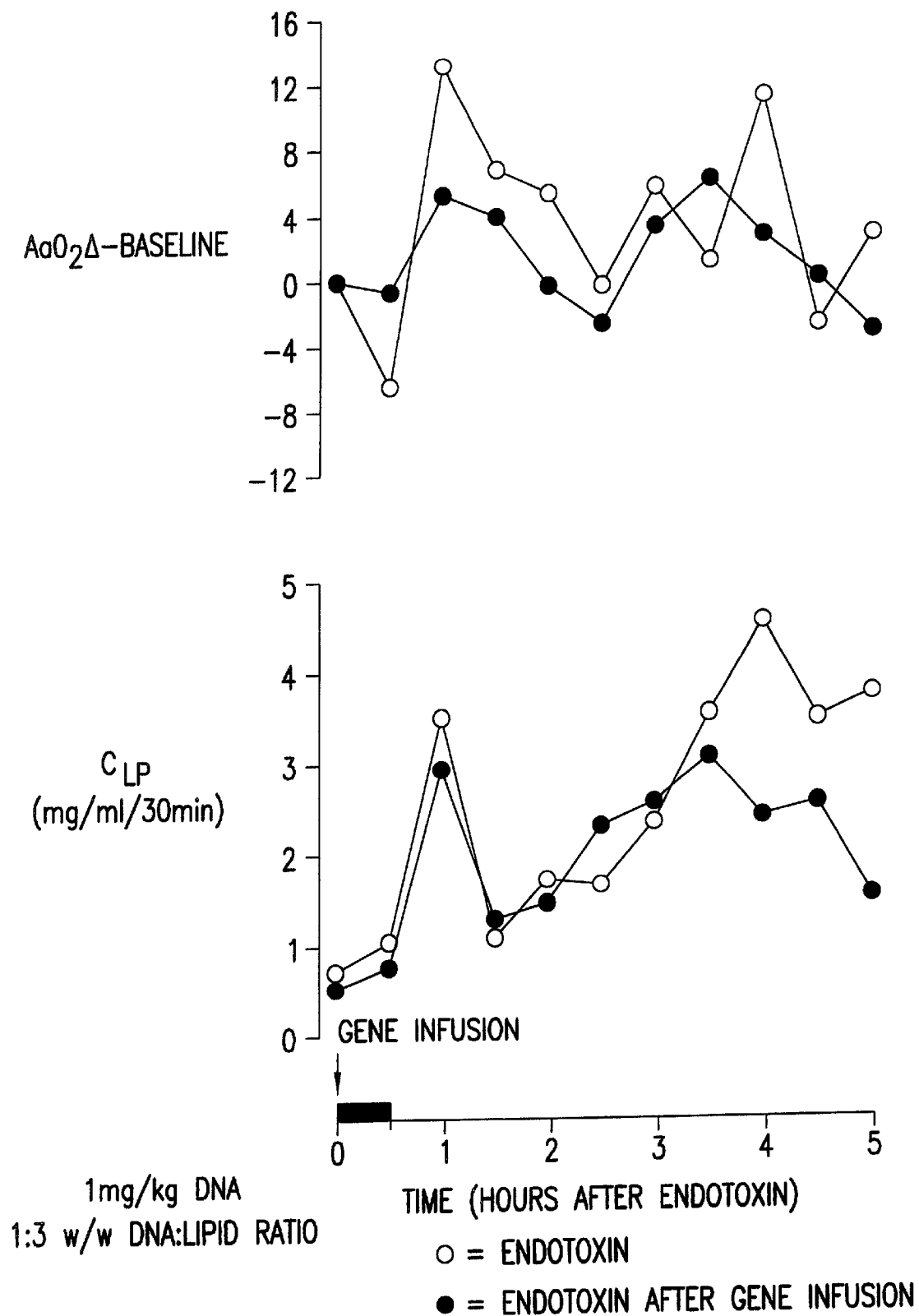
FIG. 9 shows the effects of endotoxin administration 72 hours after PGH synthase gene infusion: A slight improvement in oxygenation ($AaO_2A$-Baseline) was seen. There was attenuation in the late phase increase in lung microvascular permeability ($C_{LP}$).

FIGS. 8 and 9 show the effects of PGH gene infusion on the endotoxin response. There were no striking differences in pulmonary vascular pressures between the endotoxin study and the endotoxin study following transfection. A suggestion of improved oxygenation and a persistent improvement in lung mechanics were noted. Importantly, the late phase increase in lung microvascular permeability, the basic injury in ARDS, was reduced in the transfected animals. FIG. 9 shows lung lymph protein clearance (a measure of permeability or leakiness of the lung microvasculature) for the same studies. The persistent high permeability characteristic of the endotoxin response in this preparation was seen in the control studies, but, after transfection with PGH synthase, this increase in permeability was markedly attenuated.

These studies provide physiologic and biochemical data critical to extension of these interventions to humans. In addition, the data indicate that PGH synthase may be therapeutic in acute lung injury.

VII. Eicosanoid Metabolism in the Human Nasal Mucosa

In view of the human AAT studies reported herein, the nasal mucosa may be an ideal model for evaluating in vivo gene delivery. This is especially true for studying effects of genes which may alter arachidonic acid metabolism. Respiratory epithelium is actively involved in eicosanoid metabolism and eicosanoid metabolism in nasal epithelium is similar to respiratory epithelium from the lower airway. In order to lay the groundwork for evaluating PGH synthase gene therapy in initial human studies, important data from human nasal lavage studies has been collected. Those data demonstrate convincingly that eicosanoid metabolism is easily studied in the nose and that effects on inflammation in this relevant respiratory epithelium can be studied safely and with minimal inconvenience to the patient.

Figure 10:
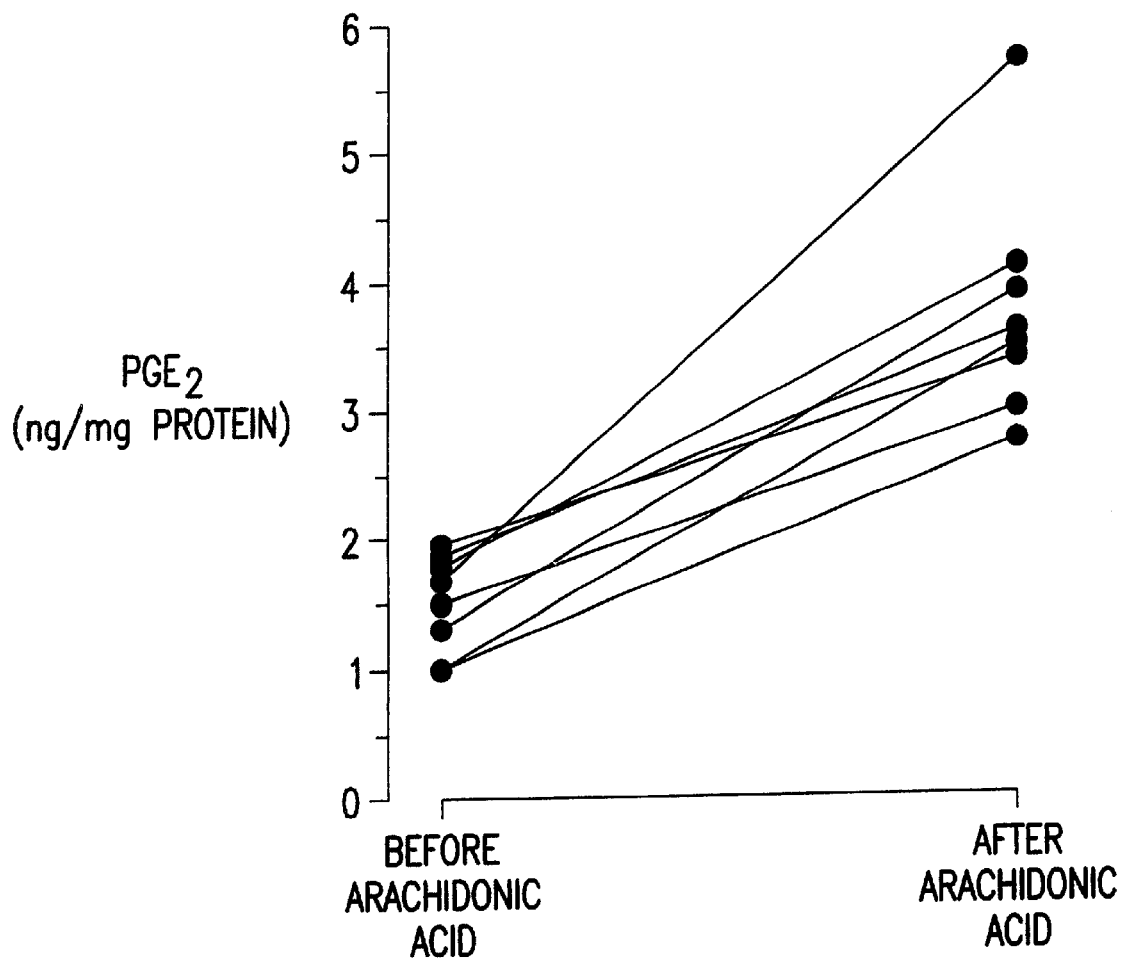
FIG. 10 shows the effects of topical arachidonic acid on $PGE_2$ production by normal human nasal mucosa.

FIG. 10 shows concentrations of prostaglandin $E_2$ ($PGE_2$), the principal prostanoid made by respiratory epithelium, in nasal lavage fluid from normal subjects prior to and after exposure to 50 uM arachidonic acid. It is apparent that, when normalized to protein content, there is a fairly constant baseline concentration of $PGE_2$ in nasal lavage fluid and that after just 10 minutes exposure to arachidonic acid, $PGE_2$ production increases. This protocol is virtually identical to that used in cultured cells to test activity of PGH synthase. This protocol in an appropriate target group of patients provides an initial test of the function of the PGH synthase gene medicine in human respiratory epithelium.

Figure 11:
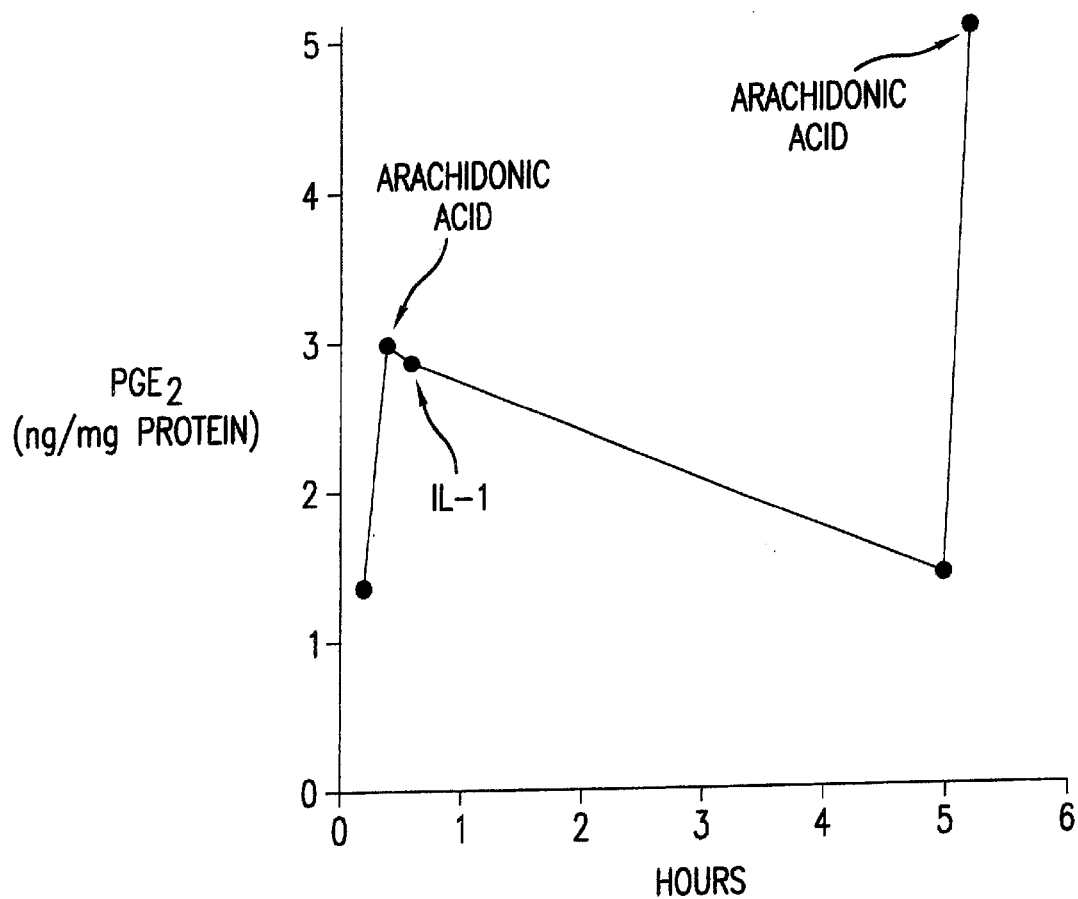
FIG. 11 shows the effects of topical IL-1 on arachidonate simulated $PGE_2$, production by normal human nasal mucosa.
Figure 12:
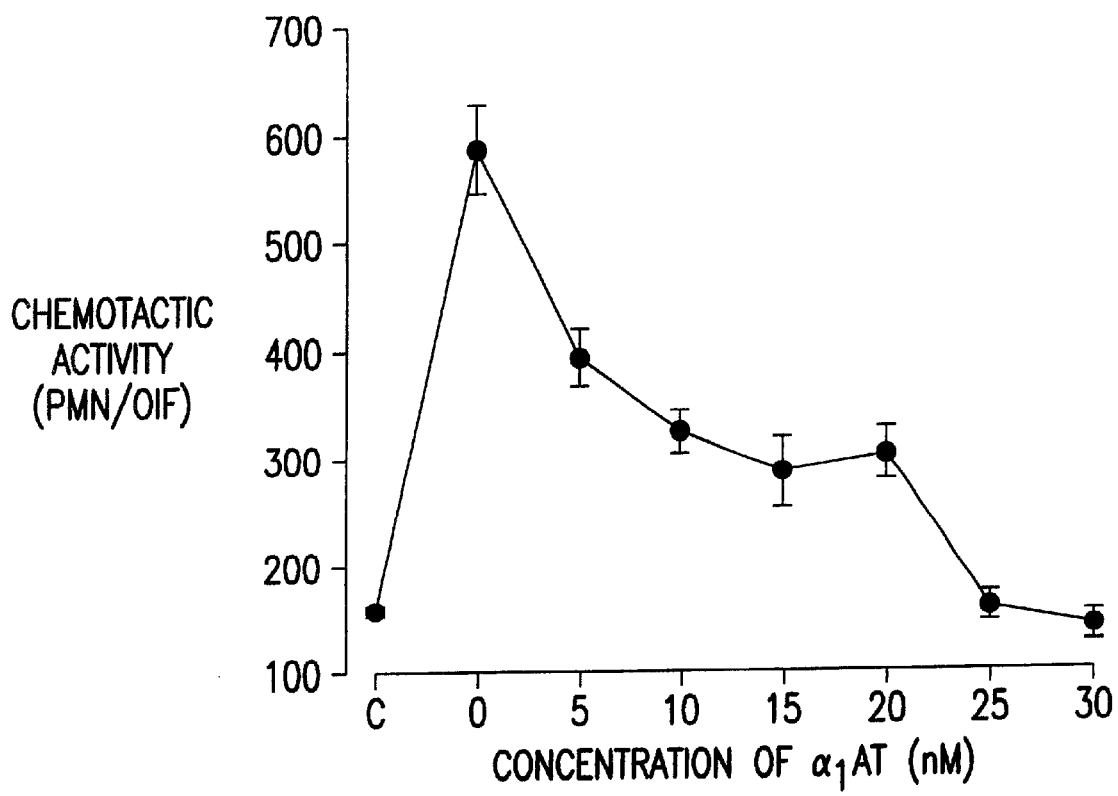
FIG. 12 shows that preincubation of 25 nM NE with various concentrations of $\alpha_1 AT$ blocks the production of chemotactic activity in the supernatant of 2CFSMEo- cells after 24 hour exposure to NE.
Figure 13:
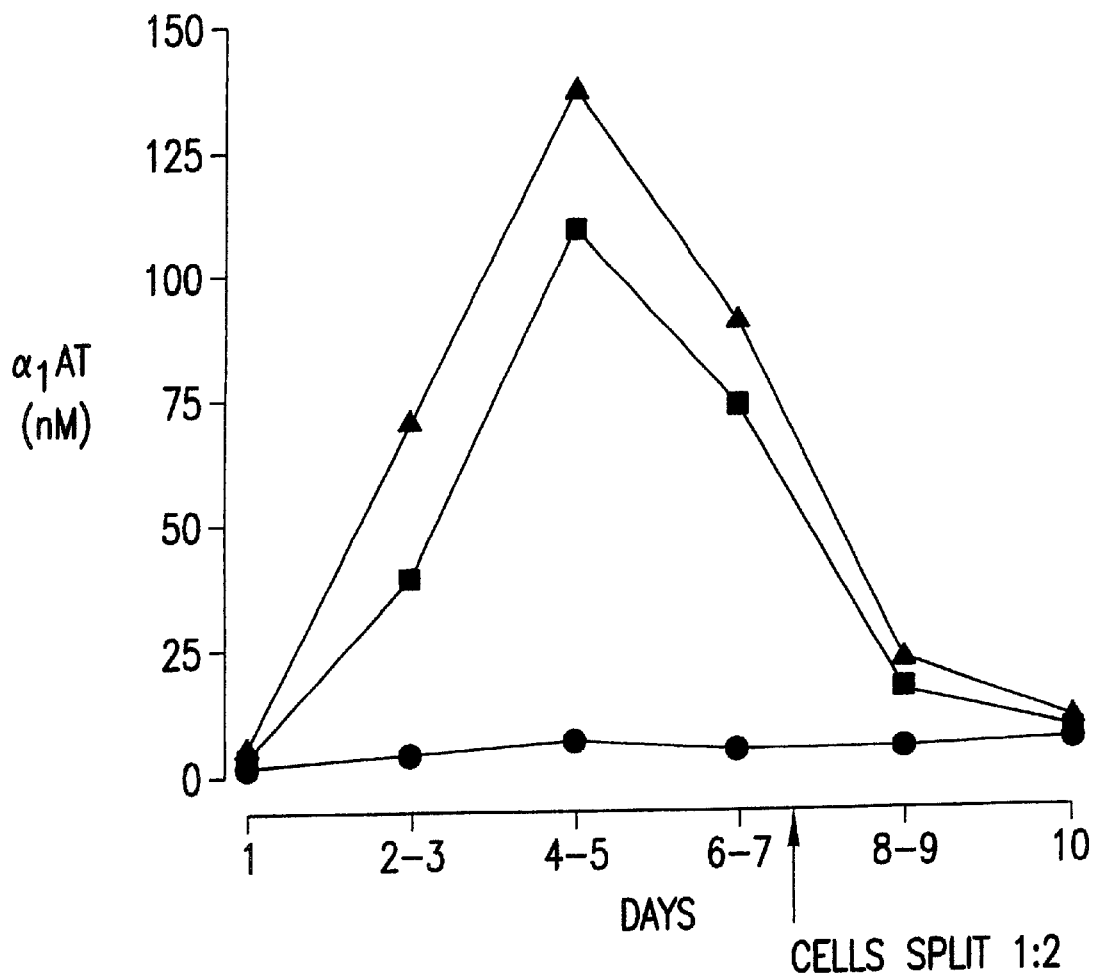
FIG. 13 shows a representative time course for the secretion of the h$\alpha$1AT gene product after transfer of the h$\alpha$1AT gene to 2CFSMEo- cells. Peak expression is seen at days 4–5.

Effects of pro-inflammatory cytokines on eicosanoid metabolism can also be studied in this model. FIG. 11 shows the $PGE_2$ production from the nasal mucosa following a brief exposure to the cytokine interleukin-1 (IL-1). Five hours after IL-1, arachidonic acid exposure resulted in a much larger increase in $PGE_2$ generation than occurred at baseline. Again, this is very similar to studies which are routinely done in cultured cells and implies induction of the cyclooxygenase enzyme by exposure to this pro-inflammatory cytokine.

VIII. Disease Targets

In view of the above, it appears that ARDS is an appropriate disease target for this gene medicine. The sheep studies show that the complexes can be delivered intravenously without evident toxicity and PGH synthase gene transfer appears to affect important variables in the endotoxin response favorably. Those skilled in the art can produce human quality reagents and perform initial studies in nasal mucosa in patients with ARDS with detailed measurements of eicosanoids, IL-1, IL-8, TNF, and assessment of inflammatory cells. Whether or not nasal epithelium reflects the same dysfunctions as epithelium lower in the respiratory tract, these studies would provide a basis for proceeding to intravenous delivery of the gene.

Interstitial pulmonary fibrosis (IPF) is an additional target for PGH synthase gene therapy. IPF is a fatal disease for which the only effective therapy right now is lung transplantation. The perpetual inflammation and lung fibrosis in this disease may be a consequence of a defect in PGH synthase so that the anti-inflammatory eicosanoid, $PGE_2$, is not produced in lung cells in sufficient quantity to suppress this abnormal response to injury.

Initial studies of both cultured lung fibroblasts and nasal lavage eicosanoid metabolism have been completed in a few patients with IPF. The nasal lavage fluid contains lower than normal concentrations of $PGE_2$. With the availability of human quality reagents, initial studies with nasal instillation of the gene in patients with IPF could be done and provide a basis for delivery of the gene to the whole lung. Because this is a desperate disease, proceeding rapidly to studies of efficacy is justified.

IX. AAT Blocks Chemotactic Activity

Human neutrophil elastase (NE) stimulates release of neutrophil chemotactic activity by a bronchial epithelial cell line and from nasal epithelial cells. NE stimulates the production of neurophil chemotactic activity by 2CFSMEo- cells, a transformed cystic fibrosis bronchial epithelial cell line. The production of chemotactic activity is dose- and time-dependent and can be blocked by preincubation of NE with $\alpha_1$ antitrypsin ($\alpha_1$AT). Incubation of the NE-stimulated culture supernatant with neutralizing concentrations of rabbit and human interleukin 8 antibody completely neutralizes the chemotactic activity.

Transfection of 2CFSMEo- cells with the eukaryotic expression vector pCMV4$\alpha_1$AT, complexed to cationic liposomes in a 1:3 wt/wt/ratio, results in at least a 10-fold increase in measured human $a_1$AT protein in culture supernatant. Detection of human $\alpha_1$AT mRNA by reverse transcriptase polymerase chain reaction in total RNA from transfected, but not untransfected cells, confirms successful gene transfer. Compared with untransfected cells, transfer of the human $\alpha_1$AT gene decreases chemotactic activity in culture supernatant and prevents cell detachment after NE exposure. This data indicate that $\alpha_1$AT gene transfer is capable of blocking at least some of the biological effects of free elastase on cultured epithelial cells.

The effect of a $\alpha_1$AT gene transfer in cystic fibrosis epithelial cells exposed to neutrophil elastase thus demonstrates that plasmid-cationic liposome-mediated h$\alpha_1$AT gene transfer to a CF bronchial epithelial cell line protects the cells from the toxic effects of elastase and inhibits elastase-stimulated release of neutrophil chemotactic activity from the epithelial cells.

Human $\alpha_1$AT gene transfer to a CF epithelial cell line, 2CFSMEo-, protects against NE-induced release of chemotactic activity and cell detachment. Transfection of the 2CFSMEo- cells with the h$\alpha_1$AT gene results in production of $\alpha_1$AT protein for 1 wk after transfection with peak expression seen at days 4 and 5. When transfected cells are exposed to NE, transfer of the h$\alpha_1$AT gene prevents NE-stimulated production of a neutrophil chemotactic factor and cell detachment.

This data (and the experimental examples and other information in Canonico et al., *Am. J. Respir. Cell Mol. Biol.* 14:348–355, 1996, incorporated herein by reference in its entirety including any drawings) indicate that Ne stimulates 2CFSMEo- calls to release a neutrophilic chemotactic factor which could be neutralized by treatment with anti-IL-8 antibody. Thus, h$\alpha_1$AT gene transfer using a plasmid-liposome delivery system protects CF bronchial epithelial cells from NE-induced cell detachment and prevents release of a neutrophil chemotactic factor, or factors, which is either IL-8 or an immunogenically related molecule. Our data do not exclude the possibility of other chemoattractants, or complement fragments.

Neutrophil elastase is capable of upregulating production of specific cytokines by bronchial epithelial cells and enzymatically inactivating others (Ruef, C. et al., *Eur. Respir. J.* 6:1429–1436, 1993). Upregulation of IL-8 or other chemoattractants may play a critical role in perpetuating the inflammatory cycle by recruiting more neutrophils into the lung airspaces. In contrast to other proinflammatory mediators, elastase-induced stimulation of cytokine production is steroid resistant (Bedard, M. et al., *Am. J. Respir. Cell Mol. Biol.* 9:455–462, 1993) but can be prevented by $\alpha_1$AT or secretory leukoprotease inhibitor (SLPI) (Nakamura, H. et al., *J. Clin. Invest.* 89:1478–1484, 1992). Because elastase's effect on epithelial cells is steroid resistant but can be inactivated by the antiproteases $\alpha_1$AT or SLPI, some type of antielastase therapy may be beneficial in the treatment of neutrophil-dominated lung diseases.

With the data accumulated implicating NE as a major agent of lung destruction in various pulmonary diseases including CF, antiprotease therapy seems rational. Although $\alpha_1$AT, the predominant antiprotease responsible for neutralizing NE, is present in the lungs from CF patients, most of it is in an inactive form (Meyer, K. C. et al. *Science* 245:1073–1080, 1989 and Suter, S. et al., *J. Infect. Dis.* 153:902–909, 1986). Because of the chronic inflammatory state in the lungs of CF patients, it is possible that $\alpha_1$AT could be oxidatively inactivated, but little data exist to support this idea. Numerous studies have indicated that $\alpha_1$AT is inactivated by proteolysis rather than oxidation and that this proteolysis is due to the overwhelming NE burden found in the lungs of CF patients (Cantin, A. et al., *Pediatr. Pulmonol.* 11:249–253, 1991 and Suter, S. and Chevalier, I., *Eur. Respir. J.* 4:40–49, 1991). Available evidence suggests that protease-antiprotease imbalance exists in the lungs of CF patients.

In contrast to $\alpha_1$AT deficiency, in which the lung disease is the result of a systemic deficiency in antiprotease protection 926), lung disease in CF is the result of a local overwhelming protease burden. Consequently, it is rational to direct antiprotease therapy locally rather than systemically. Even though aerosol therapy with SLPI or $\alpha_1$AT protein corrects the protease-antiprotease imbalance in the epithelial lining fluid (ELF) of CF patients (McElvaney, N. G. et al., *J. Clin. Invest.* 90:1296–1301, 1992 and McElvaney, M. G. et al., *Lancet* 337:392–394 (1991), twice-daily therapy is necessary and prohibitively expensive, h$\alpha_1$AT gene therapy may permit administration of the transgene at weekly or possibly longer intervals with a more cost-effective profile. In addition, by targeting the epithelial cells, h$\alpha_1$AT aerosol gene therapy may prevent elastolysis within the neutrophil-epithelial cell interface, a microenvironment which excludes the exogenously administered protein (Campbell, E. J. and Campbell, M. A., *J. Cell Biol.* 106:667–676, 1988).

Plasmid-liposome mediated delivery of the $\alpha_1 AT$ gene to CF epithelial cells in vitro protects against elastase-induced epithelial cell detachment and chemotactic release from these cells. This approach to treating the inflammatory lung injury in patients with CF or other inflammatory lung diseases could complement current therapy directed at these diseases.

III. Administration

Administration as used herein refers to the route of introduction of the composition into the body. Administration includes but is not limited to intravenous, intramuscular, systemic, subcutaneous, subdermal, topical, or oral methods of delivery. Administration can be directly to a target tissue or through systemic delivery.

In particular, the present invention can be used for administering nucleic acid for expression of specific nucleic acid sequence in cells. Routes of administration include intramuscular, aerosol, olfactory, oral, topical, systemic, ocular, intraperitoneal and/or intratracheal. A preferred method of administering compositions is by oral delivery. Another preferred method of administration is by direct injection into the cells or by systemic intravenous injection.

Transfer of genes directly has been very effective. Experiments show that administration by direct injection of DNA into joints and thyroid tissue results in expression of the gene in the area of injection. Injection of plasmids containing IL-1 into the spaces of the joints results in expression of the gene for prolonged periods of time. The injected DNA appears to persist in an unintegrated extrachromosomal state. This means of transfer is one of the preferred embodiments.

In addition, another means to administer the compositions of the present invention is by using a dry powder form for inhalation. Furthermore, administration may also be through an aerosol composition or liquid form into a nebulizer mist and thereby inhaled.

The special delivery route of any selected vector construct will depend on the particular use for the nucleic acid associated with the chitosan-based composition. In general, a specific delivery program for each chitosan-based composition used will focus on uptake with regard to the particular targeted tissue, followed by demonstration of efficacy. Uptake studies will include uptake assays to evaluate cellular uptake of the nucleic acid and expression of the specific nucleic acid of choice. Such assays will also determine the localization of the target nucleic acid after uptake, and establishing the requirements for maintenance of steady-state concentrations of expressed protein. Efficacy and cytotoxicity is then tested. Toxicity will not only include cell viability but also cell function.

The chosen method of delivery should result in cytoplasmic accumulation and optimal dosing. The dosage will depend upon the disease and the route of administration but should be between 0.1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Establishment of therapeutic levels of nucleic acid or oligonucleotide within the cell is dependent upon the rate of uptake and degradation. Decreasing the degree of degradation will prolong the intracellular half-life of the nucleic acid or oligonucleotide.

V. Direct Delivery to the Liver

Compositions of the present invention can also be used in reversing or arresting the progression of disease involving the liver, such as liver cancer. One embodiment involves use of intravenous methods of administration to delivery nucleic acid encoding for a necessary molecule to treat disease in the liver. Compositions which express a necessary protein or RNA can be directly injected into the liver or blood supply so as to travel directly to the liver.

VI. Direct DNA Delivery to Muscle

The muscular dystrophies are a group of diseases that result in abnormal muscle development, due to many different reasons. These diseases can be treated by using the direct delivery of genes with the compositions of the present invention resulting in the production of normal gene product. Delivery to the muscle using the present invention is done to present genes that produce various antigens for vaccines against a multitude of infections of both viral, bacterial, and parasitic origin. The detrimental effects caused by aging can also be treated using the compositions described herein. Since the injection of the growth hormone protein promotes growth and proliferation of muscle tissue, the growth hormone gene can be delivered to muscle, resulting in both muscle growth and development, which is decreased during the later portions of the aging process. Genes expressing other growth related factors can be delivered, such as Insulin Like Growth Factor-1 (IGF-1). Furthermore, any number of different genes may be delivered by this method to the muscle tissue.

IGF-1 can be used to deliver DNA to muscle, since it undergoes uptake into cells by receptor-mediated endocytosis. This polypeptide is 70 amino acids in length and is a member of the growth promoting polypeptides structurally related to insulin. It is involved in the regulation of tissue growth and cellular differentiation affecting the proliferation and metabolic activities of a wide variety of cell types, since the polypeptide has receptors on many types of tissue. As a result, the chitosan-based compositions of the present invention can utilize IGF-1 as a ligand for tissue-specific nucleic acid delivery to muscle. The advantage of a IGF-1/nucleic acid delivery system is that the specificity and the efficiency of the delivery is greatly increased due to a great number of cells coming into contact with the ligand/composition with uptake through receptor-mediated endocytosis. Using the nucleic acid described above in the chitosan-based compositions of the present invention with the use of specific ligands for the delivery of nucleic acid to muscle cells provides treatment of diseases and abnormalities that affect muscle tissues.

VII. Direct DNA Delivery to Osteogenic Cells

There are many other problems that occur during the aging process, but one major problem is osteoporosis, which is the decrease in overall bone mass and strength. The direct delivery of compositions of the present invention can be used to deliver genes to cells that promote bone growth. The osteoblasts are the main bone forming cell in the body, but there are other cells that are capable of aiding in bone formation. The stromal cells of the bone marrow are the source of stem cells for osteoblasts. The stromal cells differentiate into a population of cells known as Inducible Osteoprogenitor Cells (IOPC), which then under induction of growth factors, differentiate into Determined Osteoprogenitor Cells (DOPC). It is this population of cells that mature directly into bone producing cells. The IOPCs are also found in muscle and soft connective tissues. Another cell involved in the bone formation process is the cartilage-producing cell known as the chondrocyte.

A factor identified to be involved in stimulating the IOPCs to differentiate is known as Bone Morphogenetic Protein (BMP). This 19,000 MW protein was first identified from demineralized bone. Another similar factor is Cartilage Induction Factor (CIF), which also functions to stimulate IOPCs to differentiate thereby initiating cartilage formation, cartilage calcification, vascular invasion, resorption of calcified cartilage, and finally induction of new bone formation. Cartilage Induction Factor has been identified as being homologous to Transfecting Growth Factor β.

Since osteoblasts are involved in bone production, genes that enhance osteoblast activity can be delivered directly to these cells. Genes can also be delivered to the IOPCs and the chondrocytes, which can differentiate into osteoblasts, leading to bone formation. BMP and CIF are the ligands that can be used to deliver genes to these cells. Genes delivered to these cells promote bone formation or the proliferation of osteoblasts. The polypeptide, IGF-1 stimulates growth in hypophysectomized rats which could be due to specific uptake of the polypeptide by osteoblasts or by the interaction of the polypeptide with chondrocytes, which result in the formation of osteoblasts. Other specific bone cell and growth factors can be used through the interaction with various cells involved in bone formation to promote osteogenesis.

Nonlimiting examples of genes expressing the following growth factors which can be delivered to these cell types are Insulin, Insulin-Like Growth Factor-1, Insulin-Like Growth Factor-2, Epidermal Growth Factor, Transfecting Growth Factor-α, Transfecting Growth Factor-β, Platelet Derived Growth Factor, Acidic Fibroblast Growth Factor, Basic Fibroblast Growth Factor, Bone Derived Growth Factors, Bone Morphogenetic Protein, Cartilage Induction Factor, Estradiol, and Growth Hormone. All of these factors have a positive effect on the proliferation of osteoblasts, the related stem cells, and chondrocytes. As a result, BMP or CIF can be used as conjugates to deliver genes that express these growth factors to the target cells by the intravenous injection of the nucleic acid/chitosan compositions of the present invention. Using the nucleic acid described above in the chitosan-based compositions of the present invention with the use of specific ligands for the delivery of nucleic acid to bone cells provides treatment of diseases and abnormalities that affect bone tissues.

VIII. Direct DNA Delivery to the Synoviocytes

The inflammatory attack on joints in animal models and human diseases may be mediated, in part, by secretion of cytokines such as IL-1 and IL-6 which stimulate the local inflammatory response. The inflammatory reaction may be modified by local secretion of soluble fragments of the receptors for these ligands. The complex between the ligand and the soluble receptor prevents the ligand from binding to the receptor is normally present on the surface of cells, thus preventing the stimulation of the inflammatory effect.

Therapy consists of the construction of a vector containing the soluble form of receptors for appropriate cytokines (for example, IL-1), together with promoters capable of inducing high level expression in structures of the joint and composition which enables efficient uptake of this vector. This composition is then used with the nucleic acid carried by the chitosan-based compositions of the present invention. This DNA is injected into affected joints where the secretion of an inhibitor for IL-1 such as a soluble IL-1 receptor or natural IL-I inhibitor modifies the local inflammatory response and resulting arthritis.

This method is useful in treating episodes of arthritis which characterize many "autoimmune" or "collagen vascular" diseases. This method can also prevent disabling injury of large joints by inflammatory arthritis.

In addition to the above, the present invention can also be used with the following method. Current therapy for severe arthritis involves the administration of pharmacological agents including steroids to depress the inflammatory response. Steroids can be administered systemically or locally by direct injection into the joint space.

Steroids normally function by binding to receptors within the cytoplasm of cells. Formation of the steroid-receptor complex changes the structure of the receptor so that it becomes capable of translocating to the nucleus and binding to specific sequences within the genome of the cell and altering the expression of specific genes. Genetic modifications of the steroid receptor can be made which enable this receptor to bind naturally occurring steroids with higher affinity, or bind non-natural, synthetic steroids, such as RU486. Other modifications can be made to create steroid receptor which is "constitutively active" meaning that it is capable of binding to DNA and regulating gene expression in the absence of steroid in the same way that the natural steroid receptor regulates gene expression after treatment with natural or synthetic steroids.

Of particular importance is the effect of glucocorticoid steroids such as cortisone, hydrocortisone, prednisone, or dexamethasone which are the most important drugs available for the treatment of arthritis. One approach to treating arthritis is to introduce a vector in which the nucleic acid cassette expresses a genetically modified steroid receptor into cells of the joint, e.g., a genetically modified steroid receptor which mimics the effect of glucocorticoids but does not require the presence of glucocorticoids for effect. This is termed the glucocortico-mimetic receptor. This is achieved by expression of a constitutively active steroid receptor within cells of the joint which contains the DNA binding domain of a glucocorticoid receptor. This induces the therapeutic effects of steroids without the systemic toxicity of these drugs.

Alternatively, steroid receptors which have a higher affinity for natural or synthetic glucocorticoids, such as RU486, can be introduced into the joint. These receptors exert an increased anti-inflammatory effect when stimulated by non-toxic concentrations of steroids or lower doses of pharmacologically administered steroids. Alternatively, constitution of a steroid receptor which is activated by a novel, normally-inert steroid enables the use of drugs which would affect only cells taking up this receptor. These strategies obtain a therapeutic effect from steroids on arthritis without the profound systemic complications associated with these drugs. Of particular importance is the ability to target these genes differentially to specific cell types (for example synovial cells versus lymphocytes) to affect the activity of these cells.

As described in U.S. Pat. No. 5,364,791 to Vegeto, et al., entitled "Progesterone Receptor Having C Terminal Hormone Binding Domain Truncations," and U.S. application, Ser. No. 07/939,246, entitled "Mutated Steroid Hormone Receptors, Methods for Their Use and Molecular Switch for Gene Therapy," Vegeto, et al., filed Sep. 2, 1992, both hereby incorporated by reference (including drawings), genetically modified receptors, such as the glucocorticomimetic receptor, can be used to create novel steroid receptors including those with glucocortico-mimetic activity. The steroid receptor family of gene regulatory proteins is an ideal set of such molecules. These proteins are ligand activated transcription factors whose ligands can range from steroids to retinoids, fatty acids, vitamins, thyroid hormones and other presently unidentified small molecules. These compounds bind to receptors and either up-regulate or down-regulate transcription.

The preferred receptor of the present invention is modification of the glucocorticoid receptor, i.e., the glucocorticoid-mimetic receptor. These receptors can be modified to allow them to bind various ligands whose structure differs from naturally occurring ligands, e.g., RU486. For example, small C-terminal alterations in amino acid sequence, including truncation, result in altered affinity and altered function of the ligand. By screening receptor mutants, receptors can be customized to respond to ligands which do not activate the host cells own receptors.

A person having ordinary skill in the art will recognize, however, that various mutations, for example, a shorter deletion of carboxy terminal amino acids, will be necessary to create useful mutants of certain steroid hormone receptor proteins. Steroid hormone receptors which may be mutated are any of those receptors which comprise the steroid hormone receptor super family, such as receptors including the estrogen, progesterone, glucocorticoid-$\alpha$, glucocorticoid-$\beta$, mineral corticoid, androgen, thyroid hormone, retinoic acid, and Vitamin B3 receptors. Furthermore, DNA encoding for other mutated steroids such as those which are capable of only transrepression or of only transactivation are also within the scope of the above embodiment. Such steroids could be capable of responding to RU486 in order to activate transrepression.

In addition to the above, the present invention can also be used with the following method. Drugs which inhibit the enzyme prostaglandin synthase are important agents in the treatment of arthritis. This is due, in part, to the important role of certain prostaglandin in stimulating the local immune response. Salicylates are widely used drugs but can be administered in limited doses which are often inadequate for severe forms of arthritis.

Gene transfer using the present invention is used to inhibit the action of prostaglandin synthase specifically in affected joints by the expression of an antisense RNA for prostaglandin synthase. The complex formed between the antisense RNA and mRNA for prostaglandin synthase interferes with the proper processing and translation of this mRNA and lowers the levels of this enzyme in treated cells. Alternatively RNA molecules are used for forming a triple helix in regulatory regions of genes expressing enzymes required for prostaglandin synthesis. Alternatively, RNA molecules are identified which bind the active site of enzymes required for prostaglandin synthesis and inhibit this activity.

Alternatively, genes encoding enzymes which alter prostaglandin metabolism can be transferred into the joint. These have an important anti-inflammatory effect by altering the chemical composition or concentration of inflammatory prostaglandin.

Likewise, the present invention is useful for enhancing repair and regeneration of the joints. The regenerative capacity of the joint is limited by the fact that chondrocytes are not capable of remodeling and repairing cartilaginous tissues such as tendons and cartilage. Further, collagen which is produced in response to injury is of a different type lacking the tensile strength of normal collagen. Further, the injury collagen is not remodeled effectively by available collagenase. In addition, inappropriate expression of certain metalloproteinases is a component in the destruction of the joint.

Gene transfer using promoters specific to chondrocytes (i.e., collagen promoters) is used to express different collagens or appropriate collagenase for the purpose of improving the restoration of function in the joints and prevent scar formation.

Gene transfer for these purposes is affected by direct introduction of nucleic acid into the joint space where it comes into contact with chondrocytes and synovial cells. Further, the genes permeate into the environment of the joint where they are taken up by fibroblasts, myoblasts, and other constituents of periarticular tissue.

IX. Direct Delivery to the Lungs

Compositions of the present invention can also be used in reversing or arresting the progression of disease involving the lungs, such as lung cancer. One embodiment involves use of intravenous methods of administration to delivery nucleic acid encoding for a necessary molecule to treat disease in the lung. Compositions which express a necessary protein or RNA can be directly injected into the lungs or blood supply so as to travel directly to the lungs. Furthermore, the use of an aerosol or a liquid in a nebulizer mist can also be used to administer the desired nucleic acid to the lungs. Finally, a dry powder form can be used to treat disease in the lung. The dry powder form is delivered by inhalation. These treatments can be used to control or suppress lung cancer or other lung diseases by expression of a particular protein encoded by the nucleic acid which is chosen to be delivered.

Additional organs, tissues, cavities, cell or cells, spaces for the administration of the molecules mentioned herein may be found in "Nucleic Acid Transporters for Delivery of Nucleic Acids into a Cell"; Smith et al., U.S. patent application Ser. No. 08/484,777, filed Dec. 18, 1995, incorporated herein by reference in its entirety including any drawings.

EXAMPLES

The present invention will be more fully described in conjunction with the following specific examples which are not to be construed in any way as limiting the scope of the invention.

Materials and Methods

Preparation of pCMV4$\alpha_1$AT Vector. Production and design of the plasmid used for this study, pCMV4$\alpha_1$AT, has been previously described in International Patent Application, Publication Number WO 92/19730, which is hereby incorporated herein by reference in its entirety, including any drawings.

Isolation of Neutrophils for Chemotaxis Assay. A 30 ml sample of heparinized whole blood was collected from a single healthy adult donor into syringes. The collected blood was mixed 1:1 with normal saline, and each 30 ml of blood was layered over 15 ml Ficoll-Paque (specific gravity 1.077) (Pharmacia, Piscataway, N.J.) and centrifuged at 800×g for 30 min. After centrifugation, the top layer and interface were removed and discarded. The cell pellet was resuspended in phosphate-buffered saline followed by centrifugation at 400×g. The washed cell pellet was mixed 1:1 with 3% T-500 dextran (Pharmacia) prepared in isotonic saline and allowed to sediment for 1 hour. The upper fraction, containing predominantly neutrophils, was removed and centrifuged at 400×g.

To lyse the remaining erythrocytes, the resulting pellet was treated for 60 s with 0.2% saline and then made isotonic by adding 1.8% saline (1:1, vol/vol). The cells were washed, resuspended in Dulbecco's modified Eagle's medium (DMEM)-f/12 (Gibco/BRL, Grand Island, N.Y.) in polypropylene tubes to prevent cell adherence, and placed on ice. The total cell yield was determined by counting a portion of the final suspension in a hemocytometer. This method yielded 5 to $8 \times 10^7$ cells/30 ml whole blood. Visibility was in excess of 95% as measured by trypan blue dye exclusion. The differential cell count was determined by staining cytospin preparations with Diff-Quik (Baxter Scientific Productions, McGaw Park, Ill.) and counting across the entire slide. The differential was consistently greater than 93% neutrophils, with <1% monocytes, approximately 5% eosinophils, and 2% lymphocytes.

Measurement of Neutrophil Chemotactic Activity. Isolated human neutrophils from a single donor were used as responding cells. These cells were suspended in DMEM-F/12 culture medium at a concentration of $1 \times 10^4$ polymorphonuclear leukocytes/ml. Chemotactic assays were performed utilizing the multiwell microchamber as previously described (Falk, W. et al., *J. Immunol. Methods* 33:239–247, 1980 and McCain, R. et al., *Am. J. Respir. Cell Mol. Biol.* 8:28–34, 1993). Briefly, neutrophils were placed in the upper chamber, and the potential chemoattractant was passed in the lower chamber separated by polyvinylpyrrolidone (PVP)-free polycarbonate filters with 3-$\mu$m pore diameters. Cell migration took place during a 30-min incubation period in a humidified incubator at 37° C. in a 5% $CO_2$/air atmosphere.

After incubation, the filters were fixed and stained with Diff-Quik, and the neutrophils that had migrated through the filter were counted under oil immersion (×1,000) light microscopy. Chemotactic activity was expressed as the mean of triplicate determinations of the number of neutrophils that migrated toward the tested chemoattractant in 10 oil immersion fields. Fresh DMEM-F/12 was used as a negative control; IL-8 was used as a positive control. Cell culture supernatant was treated with neutralizing concentration of rabbit anti-human IL-8 serum (Upstate Biotechnology inc., Lake Placid, N.Y.) to assess the contribution of IL-8 to the chemotactic bioactivity. A 1:5,000 dilution of rabbit anti-human IL-8 serum was added to each sample and incubated for 1 h at 37° C., which is sufficient to neutralize biologically relevant concentrations of natural IL-8 (McCain, R. et al., *Am. J. Respir. Cell Mol. Biol.* 8:23–34, 1993). The nonimmune rabbit serum used as a control had no effect on chemotaxis of neutrophils, nor did it alter the chemotactic activity of stimulated culture supernatant.

Cell Culture Techniques. The immortalized human CP bronchial epithelial cell line 2CFSMEo- was used in these experiments. The cell line was a gift from Dr. Ray Frizzell (University of Alabama, Birmingham) (Cozens, A.L. et al., *Proc. Natl. Acad. Sci USA* 89:5171–5175, 1992). These cells were maintained on a plastic surface in DMEM-F/12 with 10% feral bovine serum (Summit Biotechnology, Ft. Collins, Co.). Confluent cell cultures were removed from passage with 1% trypsin-EDTA. For the NE dose-response and the NE:$\alpha_1$AT dose-response experiments, $4 \times 10^5$ cells were placed in serum-conditioned medium onto 30-mm, 6-multiwell tissue culture wells (Becton Dickinson, Lincoln Park, N.J.). In some experiments, in an effort to minimize interwell variability during gene transfer, the cells were plated onto 100-mm tissue culture dishes (Corning Glass Works, Corning, NY) and transfected with pCMV4$\alpha_1$AT or pCMV4 complexed to cationic liposomes. These cells were harvested 3 days after transfection, and $4 \times 10^5$ of the transfected cells were subcultured onto the six multiwell tissue culture plate for further experiments.

Experimental Protocols

Neurophil Elastase Exposure on Untransfected 2CFSMEo- Cells. To determine neutrophil chemotactic activity and immunoreactive levels of IL-8 produced by 2CFSMEo- cells following NE exposure, a time- and dose-response experiment was performed prior to the gene transfer experiments. 2CFSMEo- cells were plated onto six-multiwell plates as described above. At 24 h after the wells were seeded, the cells were washed 3 times with serum-free media, and serum-free media was added to the cells (see below). Concentration of NE from 5 to 25 nM were added to the cells for 24 hours. After determination of the optimum dose, a time course was performed to determine the time of peak chemotactic activity production in response to NE. After the time- and dose-response to Ne were established, 25 nM NE was incubated with concentrations of h$\alpha_1$AT protein (Prolastin; Miles Inc., Elkhart, Ind.) ranging from 0 to 50 nM to determine the effect of NE neutralization on chemotaxis.

Protocol of h$\alpha_1$AT Gene Transfer. Various amounts of pCMV4$\alpha_1$AT or pCMV4 were complexed to synthetic cationic liposomes (Lipofectin, Bethesda Research Laboratories, Gaithersburg, Md.) in a 1:3 wt/wt ratio. In preliminary studies, a 1:3 wt/wt ratio of plasmid to liposomes achieved maximal transgene expression for this plasmid. The plasmid was brought up to equal volume with the cationic liposome by the addition of sterile water. The liposomes were added to the DNA, and complex formation occurred at room temperature. The plasmid-liposome complexes were added to 2CFSMEo- cells in the presence of serum-containing medium (day 0). Then, 24 h later (day 1), the media was removed and fresh media was added. Subsequently, the media was changed at either 24- or 48-h intervals. All transfection experiments were done in triplicate.

Time Course of Gene Expression. To determine an optimal time to expose the cells to NE with respect to transgene expression, a time course of gene expression was performed. During the NE exposure to transfected 2CFSMEo- cells, media was left on the cells for 48 h (see below). Therefore, after the media was removed 24 h following transfection, h$\alpha_1$AT secretion was determined in 48-h intervals.

h$\alpha_1$AT RNA Analysis. To analyze for h$\alpha_1$AT with mRNA, 2CFSMEo- cells in 100-mm tissue culture dishes were transfected with pCMV4$\alpha_1$AT-liposome complexes. At day 3 after transfection, RNA was isolated using RNA STAT-60 (TEL-0TEST "H"; Friendswood, Tex.). RNA analysis was performed directly from gene transfer experiments in the 100-mm culture dishes to provide a large cell population for RNA isolation. The quality of the RNA was determined by electrophoresis in a 1% agarose denaturing gel; the quantity was determined by optical density (Ultrospec Plus; Pharmacia, Piscataway, N.J.). Reverse transcriptase polymerase chain reaction (RT-PCR) was performed using 2 $\mu$g of RNA from both control and transfected cells. To ensure that the RT-PCR only amplified RNA, 2 $\mu$g of PCMV4$\alpha_1$AT plasmid was used as a negative, internal control. Prior to RT, the RNA and the PCMV4$\alpha_1$AT plasmid control were incubated with DNAse (Promega, Madison, Wis.) at 37° C. for 15 min to digest any DNA that may have been present. Immediately following the 37° C. incubation, the DNAse was heat-inactivated at 65$\alpha_1$AT C for 15 min.

First-strand cDNA synthesis was performed using a First-Strand cDNA Synthesis kit (Pharmacia). After first-strand cDNA synthesis was complete, the samples were diluted 1:5; two 20-mer primers located 534 bases apart were added with 200 μMdNTP and Taq polymerase (Boehringer Mannheim, Indianapolis, Ind.). PCR was performed for 35 cycles (denatured at 95° C., annealed at 45° C., extended at 72° C.). The resultant 534-base pair PCR product was electrophorased through a 1% agarose gel and visualized by staining with ethidium bromide.

As a positive control for PCR, 2°g of PCMV4$\alpha_1$AT plasmid was processed in an identical manner to the RNA samples except without DNAse treatment.

NE Treatment of Transfected 2CFSMEo- Cells. Prior to the addition of human NE (Elastin Products Co., Owensville, Mo.), the cells were washed with serum-free media 3 times. After the washes, serum-free media was placed on the cells and NE was added 24 h later. This was done for two reasons: First, serum-free media was used to minimize any potential neutralization of h$\alpha_1$AT or Ne with serum proteins. Second, a 24-h interval between the addition of fresh media and the addition of NE provided an opportunity for the transfected cells to replenish the supernatant with h$\alpha_1$AT before adding NE. Then, 24 h after the addition of NE, the supernatant was collected and centrifuged at 13,000×g for 5 min to remove any cellular debris. The supernatant was stored at −70° C. for future measurement of h$\alpha_1$AT and IL-8 by ELISA and for chemotactic activity. In addition, the effect of transfection and NE treatment on cell morphology was evaluated utilizing an inverted-phase microscope.

Statistical Analysis

Data were evaluated with analysis of variance followed by contrast analysis of planned comparisons and, where appropriate, post hoc comparisons by the Scheffé test.

Example 1
Method of Plasmid Construction

The pCMV4-$\alpha_1$-antitrypsin plasmid is constructed by linkerprimer polymerase chain reaction (LP-PCR).

The coding sequence of $\alpha_1$-antitrypsin is inserted into the PCMV4 expression vector. This method consists of synthesizing two oligonucleotide primers (20–30 nucleotides in length). One oligonucleotide is homologous to the 5' untranslated region immediately upstream (5') of the initiation codon and the second oligonucleotide is complementary to the 3' untranslated region immediately downstream (Y) of the stop transcription codon. Both oligonucleotides have a one or two base substitution which creates a unique restriction enzyme site in the untranslated regions of the amplified gene. The 5' and 3' oligonucleotides were designed such that the created restriction enzyme site is approximately 8 nucleotides downstream from the 5' end of the oligonucleotide. Both of these requirements are critical, the former to insure a restriction enzyme site which is recognizable and cleavable and the latter to insure that the reading frame of the gene is not altered.

Except for the cDNA for $\alpha_1$-antitrypsin and the 3'UTR of human growth hormone which were sequenced using the Sanger dideoxy method, the sequence is compiled using the current version of Genbank as source of the sequence information. The reading frame of the $\alpha_1$-antitrypsin gene is amplified using Vent DNA polymerase, 100 ng of target DNA, a programmable temperature cycler, and standard reaction conditions (denaturing at 93.5°, annealing at 56° and extension at 75°). Vent DNA polymerase is used because it has a 3' to 5' proofreading activity in addition to enhanced stability at high temperature and a highly specific and processive 5' to 3' DNA polymerase activity. After PCR amplification, the unique restriction sites were cleaved with the appropriate restriction enzymes (ClaI; SmaI), the amplified gene is separated from the small fragments released by the action of the restriction enzymes and from unincorporated primers and nucleotides by gel filtration through a S-400 spin column. The amplified genes which now had cloning sites on each end were ligated into PCMV4 which had been previously cleaved with the same restriction enzymes which were utilized to prepare the cloning sites on the amplified gene.

After ligation, the pCMV4-$\alpha_1$-antitrypsin construct is transfected into fresh competent bacteria (*E. coli* NM522). The competent bacteria is prepared by standard methods. A single bacterial colony is selected from a 14-day old refrigerated storage plate. The colony is placed in 30 ml of LB broth and grown to an O.D. of 0.600 at 600 nm. The bacterial suspension is cooled on ice for 10 min and the bacteria were collected by centrifugation for 10 min at 1,650×g. The bacterial pellet is resuspended in 10 ml transformation buffer, kept on ice for 10 min, and collected again by centrifugation as above. The pellet is resuspended in 2 ml transformation buffer; 70 μl of dimethylsulfoxide (DMSO) is added and the sample kept on ice for 10 min; 70 μl of 1M dithiothreitol (DDT) in KAc buffer is added and the sample incubated for 5 min before a second 70μ aliquot of DMSO added.

A 300 μl aliquot of the bacteria is removed and an aliquot of the ligated DNA added; this mixture is incubated on ice for 45 min, heatshocked at 42° C. for 3.5 min, diluted to 1 ml with 2XYT medium and incubated at 37° C. for 1 hour. Multiple aliquots of this mixture (routinely 25, 50, and 200 μl) were plated separately on LB agar plates containing 50 μg/ml of ampicillin which provides selection pressure for bacteria containing the pCMV4 construct. The plasmid carries the gene for arnpicillin resistance. After the bacteria which harbor the plasmid have grown into distinct colonies several of the colonies are grown up as individual 5 ml liquid cultures in 2XYT medium containing ampicillin. Aliquots, of the liquid cultures are stored frozen at −70° C.

Example 2
Small-scale Preparation (2 L) of Plasmid

A pellet of frozen stock (*E. coli* strain NM522 containing PCMV4-$\alpha_1$-antitrypsin) is streaked onto an LB agar plate containing 50 μg/ml ampicillin with a sterile platinum loop. The plate is incubated at 37° C. overnight. Two liters of 2XYT medium containing ampicillin are inoculated with a single colony from this plate. Following overnight incubation at 37° C. the bacteria are collected by centrifugation for 20 min at 10,000×g. The bacterial pellet is processed and purified using the Quiagen Mega-prep kit according to the manufacturer's protocol. The isolated plasmid is precipitated with ethanol and resuspended in sterile water. Demineralized water is treated with a Millipore Milli-Q water purification system until conductivity (built-in) is 18 mOhm or less, filtered through a 0.22μ Millipore depth filter, and then steam autoclaved. Samples are stored at −20° C. in 1 ml aliquots.

Glassware, centrifuge bottles, microfuge tubes, magnetic stir bars, water (see above), and bacterial growth media are Example 3

Scaled-up Preparation (100 L) of Plasmid

A large batch of plasmid (1.3–1.4 kg cells) is prepared by the University of Iowa Large Scale Fermentation Facility, 3-670 Bowen Science Building, Iowa City, Iowa 52242 (Lacy Daniels) according to the following protocol.

I. Summary

One 100 liter fermentor run is performed with *E. coli* strain NM522-PCMV4-α1-antitrypsin grown in medium composed of a mixture of Luria Broth Base and Terrific Broth. An inoculum is prepared from an isolated colony, scaled up by growth on plates and grown finally in Ferribach flasks for the inoculum. All media contain originally ca. 75–100 μg ampicillin/ml. Cells are harvested with a Sharples continuous centrifuge after absorbance reached a near maximal point. Cells are frozen directly in liquid nitrogen and shipped on dry ice. Cell yields are usually 1.3–14. kg wet cells per fermentor run.

ii. Inoculum Preparation

The vials received from Dr. Canonico, Vanderbilt University, are streaked onto Luria agar plates containing 100 μg ampicillin/ml. In a laminar flow cabinet, one isolated colony is used to streak a lawn onto one whole plate of the same type; 8 plates are prepared. Plates are incubated overnight at ca. 35–37° C., and then, in the laminar flow cabinet, removed aseptically by cotton swab into a flask containing 50 ml of sterile Luria broth containing 20% glycerol. This solution is transferred to a series of sterile small plastic storage vials which are placed in a −45° C. freezer for future convenient use as inoculum.

For a 100 liter fermentor, six vials are used to inoculate six 2.8 liter Fernbach flasks (500 ml Luria Broth base media in each flask +100 μg ampicillin/ml). The flasks are incubated shaking at ca. 150 rpm at ca. 35–37° C. for 9 hours. Flasks are combined into two containers aseptically and inoculation is done by peristaltic pump using a sterile stainless steal probe connected with a sterile silicone rubber tubing leading into the top of the fermentor vessel via a septum port.

iii. Fermentor Medium 20 g/L Luria Broth Base 15 g/L Terrific Broth powder

75 μg/ml. ampicillin added as liquid to sterile medium 3 ml/L glycerol 10 ml Sigma Antifoam B iv. Fermentor The fermentor is a 100 liter working volume B. Braun 100D. It is sterilized in place at 121° C. using steam; the medium is heated at 121° C. for 45 min during which all critical connections and components are also sterilized. External items are sterilized in an autoclave. Incoming air and exiting gas are sterilized by filtration. Fermentation conditions are:

37° C.

300 rpm (16 cm Rushton-type impeller)

air at 30 liters/min (0.3 vvm); internal pressure 0.3 bar pH monitored with internal pH probe; confirmed with a lab pH meter; pH is initially 6.8 and varies between 6.7 and 7.0 (no pH control is used since there is predictably little change)

dissolved oxygen is monitored with an oxygen probe, and varied between 100% of saturation at the start to a minimum of ca. 67% during the run an automatic foam control system and silicone antifoam is provided to control foaming problems, but generally very little foam is produced during the run; a total of ca. 20–40 ml of Sigma Antifoam B is used during the run.

Culture samples are taken each 1–2 hours to follow growth by monitoring the absorbance at 600 nm. Samples are removed via a sample port that is sanitized with steam following each sampling. A plot of a typical growth curve is appended. The initial medium has 75 μg/ml ampicillin; additional ampicillin is added after approximately 3 and 6 hours to make an additional 25 or 50 μg/ml, respectively.

v. Harvesting

When cells reach near maximum absorbance (after ca. 5–7.5 hours of fermentor growth), vessel cool-down begins and harvesting is initiated when the medium reaches 25° C.; cooling continues during harvesting and the contents reach 17° C. by the end of harvesting. Harvesting is done with a Sharples tubular bowl continuous centrifuge capable of harvesting a maximum of ca. 1.6 kg wet cells. The cells are fed via a Tygon hose from the sample port into the bottom of the rotating stainless steel bowl. When all of the vessel contents are centrifuged, the centrifuge bowl is removed and the contents removed by spatula and placed as chunks of a paste into liquid nitrogen. The frozen chunks are then transferred to clean plastic bottles and kept in a −45° C. freezer until they are shipped on dry ice. Cell yields per fermentor are 1.3–1.4 kg.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed:

1. A method of treating a mammal exposed to endotoxin, comprising delivering a nucleic acid molecule encoding $\alpha_1$ antitrypsin to a lung cell in the mammal, wherein the lung cell produces $\alpha_1$ antitrypsin encoded by the nucleic acid molecule, thereby treating the mammal exposed to endotoxin.

2. A method of inhibiting an increase in pulmonary vascular resistance due to the presence of endotoxin in a mammal, comprising delivering a nucleic acid molecule encoding $\alpha_1$ antitrypsin to a lung cell in the mammal, wherein the lung cell produces $\alpha_1$ antitrypsin encoded by the nucleic acid molecule, thereby inhibiting an increase in pulmonary vascular resistance in the mammal.

3. The method of claim 1 or 2, wherein the nucleic acid molecule encoding $\alpha_1$ antitrypsin is associated with a positively charged liposome.

4. The method of claim 3, wherein the positively charged liposome is a 1:1 (weight/weight) liposome formulation of N-[1-(2,-dioleyloxy)propyl]-N,N,N-trimethylammonium chloride (DOTMA) and dioleoyl phosphatidylethanolamine (DOPE).

5. The method of claim 1 or 2, wherein the lung cell is an endothelial lung cell, a smooth muscle cell adjacent to an endothelial lung cell, or a lung parenchymal cell.

6. The method of claim 1 or 2, wherein the $\alpha_1$ antitrypsin is human $\alpha_1$ antitrypsin.

7. The method of claim 1 or 2, wherein the nucleic acid molecule encoding $\alpha_1$ antitrypsin is a DNA molecule in operable association with a promoter.

* * * * *